(12) United States Patent
Iqbal et al.

(10) Patent No.: US 8,765,453 B2
(45) Date of Patent: Jul. 1, 2014

(54) AUTOMATIC SAMPLE STAINING SYSTEM

(75) Inventors: Shazi S Iqbal, Danville, CA (US);
Steven M Montgomery, Los Angeles, CA (US); Ronald Chang, Redwood City, CA (US); Gregory E Mote, Los Angeles, CA (US); Douglas B Dority, Santa Cruz, CA (US); Jeffrey S Ross, Lebanon Springs, NY (US)

(73) Assignee: SYFR, Inc., Danville, CA (US)

( * ) Notice: Subject to any disclaimer, the term of this patent is extended or adjusted under 35 U.S.C. 154(b) by 0 days.

(21) Appl. No.: 13/330,472

(22) Filed: Dec. 19, 2011

(65) Prior Publication Data
US 2012/0329140 A1    Dec. 27, 2012

Related U.S. Application Data

(62) Division of application No. 12/135,925, filed on Jun. 9, 2008.

(51) Int. Cl.
*G01N 1/31*    (2006.01)
*G01N 35/00*    (2006.01)

(52) U.S. Cl.
CPC .......... *G01N 1/312* (2013.01); *G01N 35/00029* (2013.01); *G01N 2035/00792* (2013.01)
USPC ........................ 435/286.1; 435/283.1; 436/46

(58) Field of Classification Search
CPC ............................................ G01N 2035/00792
See application file for complete search history.

(56) References Cited

U.S. PATENT DOCUMENTS 6,534,008 B1 *   3/2003   Angros ............................. 422/64
6,746,851 B1 *   6/2004   Tseung et al. ............... 435/40.5

* cited by examiner

*Primary Examiner* — Yelena G Gakh
*Assistant Examiner* — Michelle Adams
(74) *Attorney, Agent, or Firm* — James R Bell; Mark P Kahler

(57) ABSTRACT

Provided is a system and method for staining of one or more samples, including providing one or more self-contained sample processing receptacles, each of the one or more self-contained sample processing receptacles configured to be inserted into an auto-staining instrument; and enabling one of one or more staining procedures appropriate for the one or more samples as a function of a choice of self-contained sample processing receptacle, each of the one or more self-contained sample processing receptacles configured to process each inserted sample of the one or more samples within the self-contained sample processing receptacle.

4 Claims, 19 Drawing Sheets

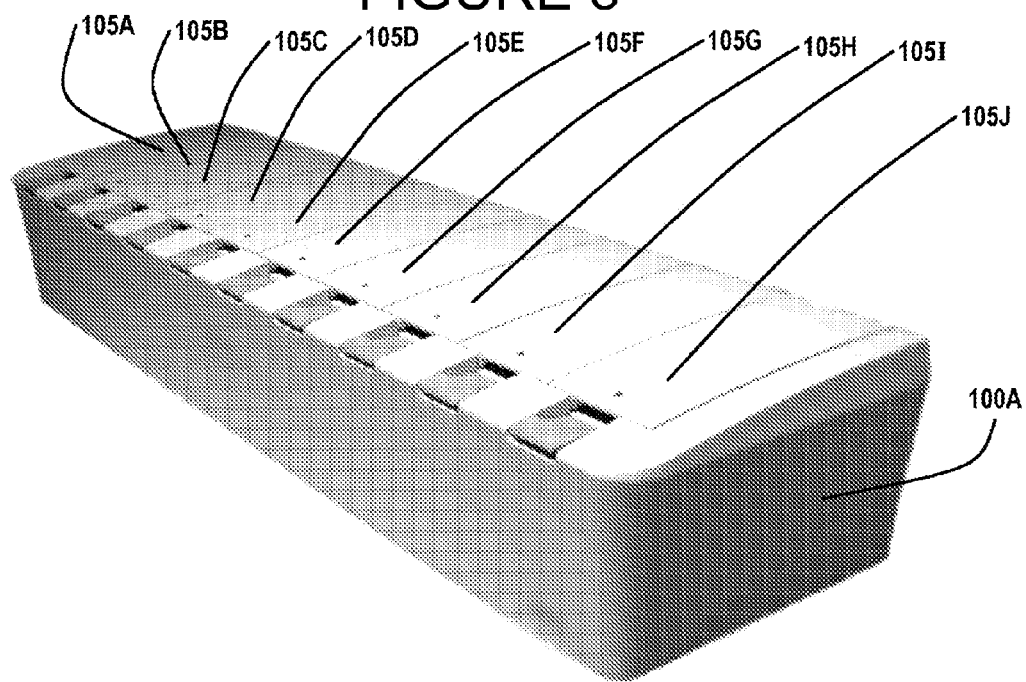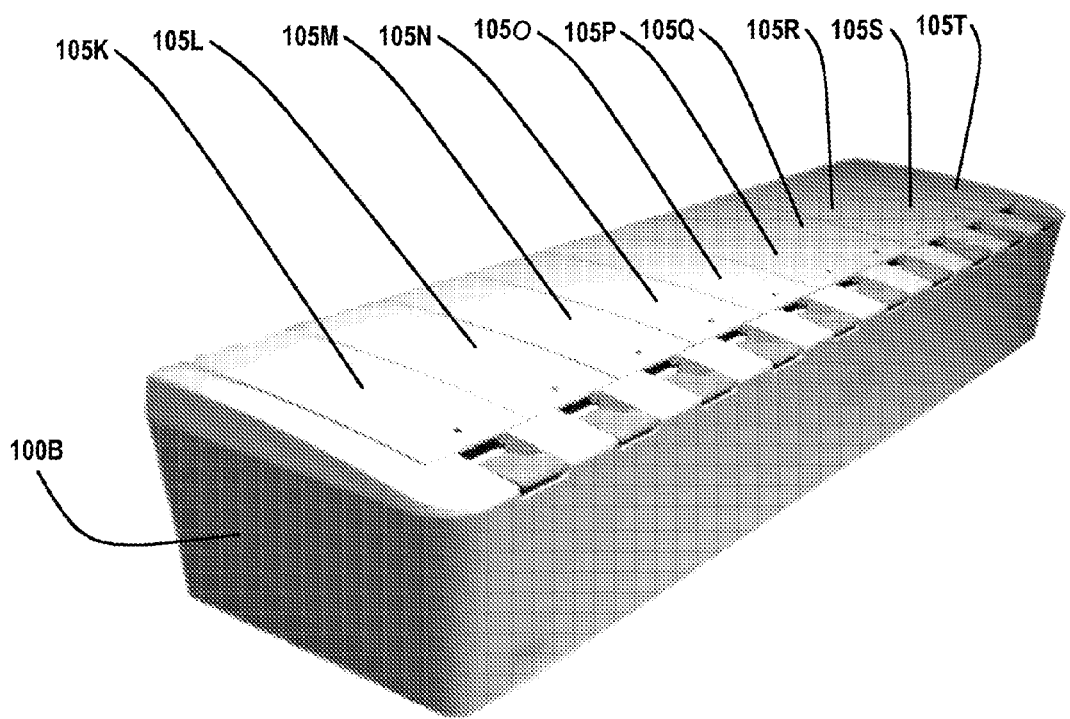

FIGURE 7
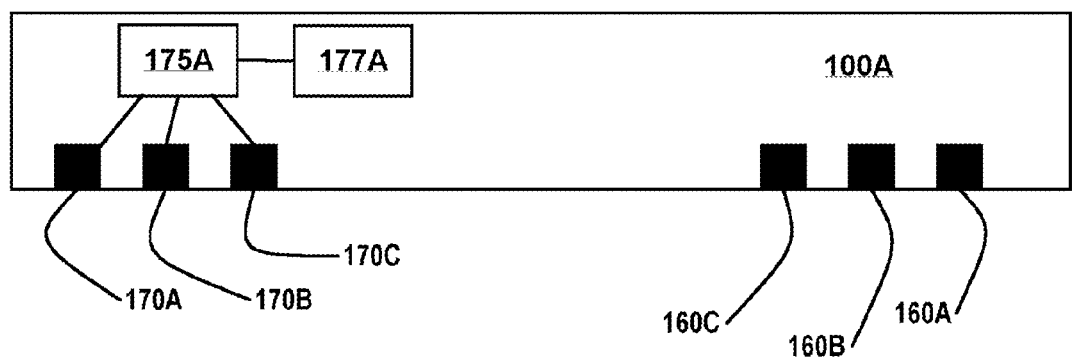
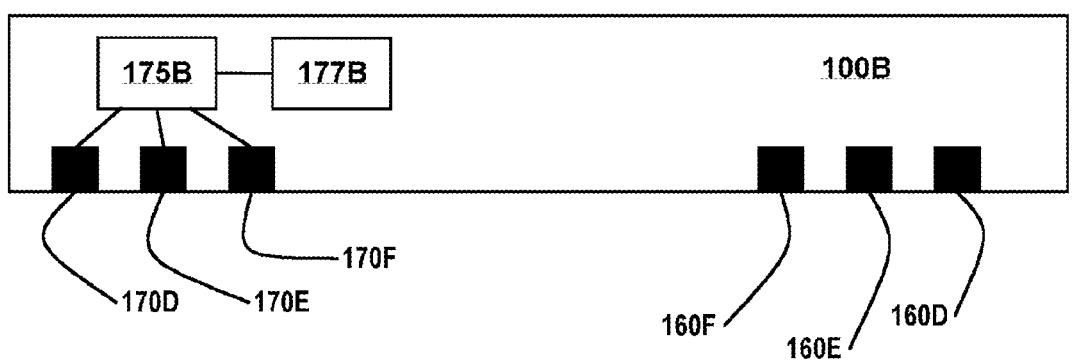
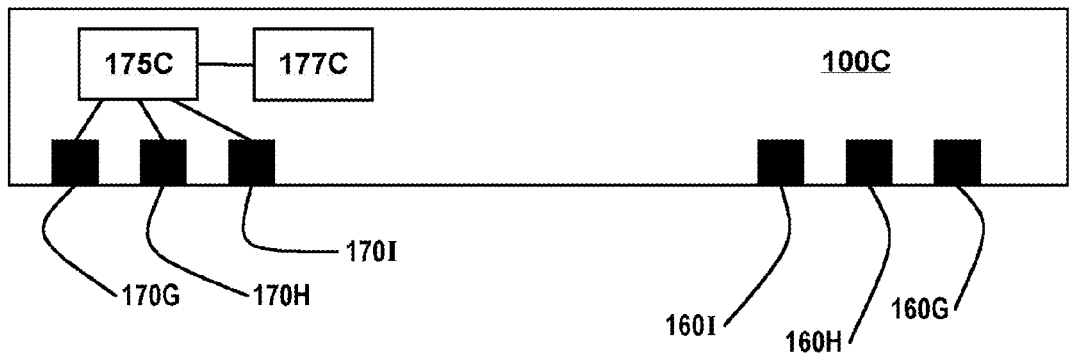

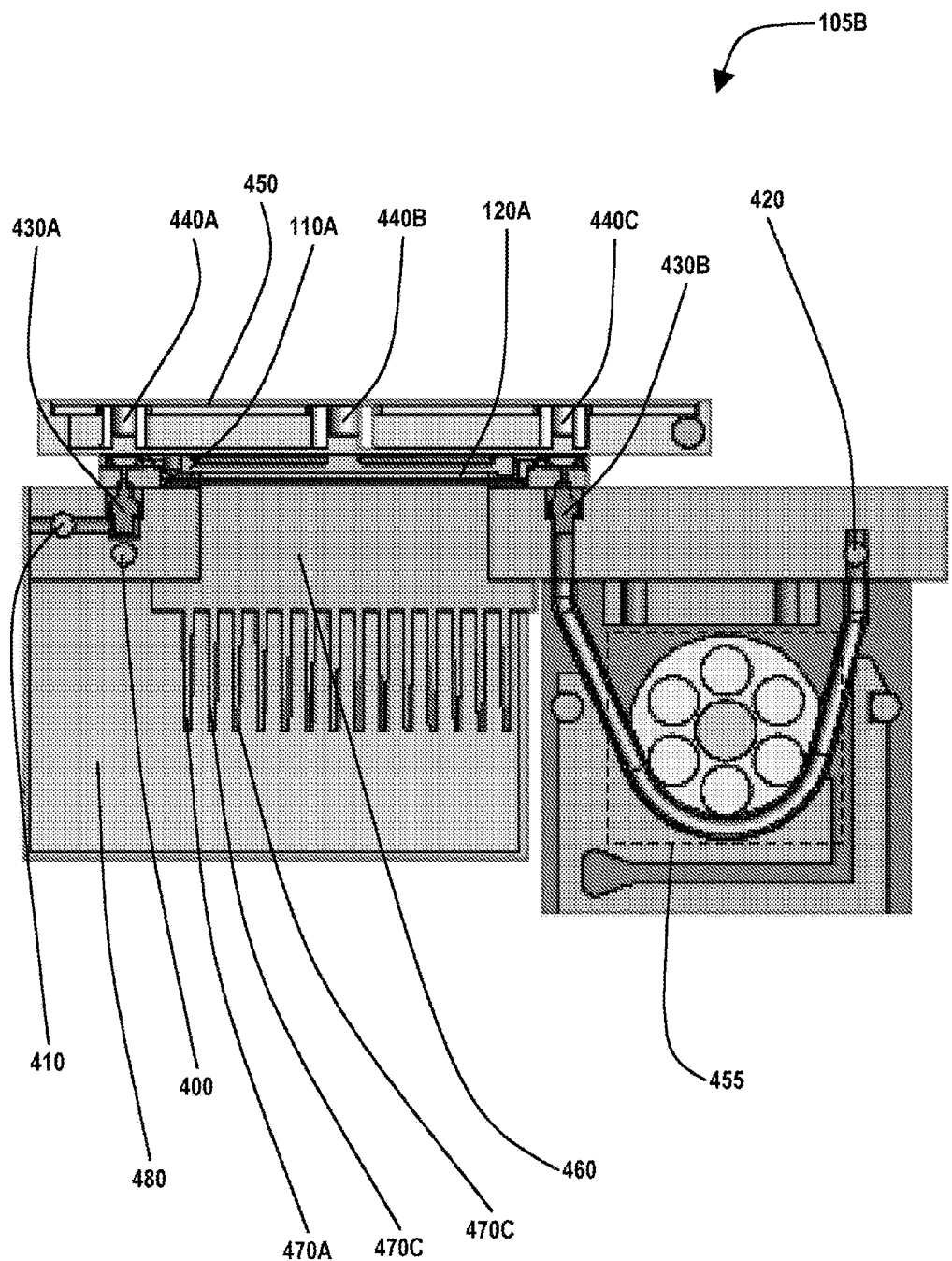

FIGURE 15 providing one or more self-contained sample processing receptacles, each of the one or more self-contained sample processing receptacles configured to be inserted into an auto-staining instrument 1510 providing one or more modules within the auto-staining instrument, each module operable to receive one of the one or more self-contained sample processing receptacles and independently couple each self-contained sample processing receptacle to the auto-staining instrument 15102 providing within each of the one or more self-contained sample processing receptacles a chamber adapted to receive and enclose at least one of the one or more samples, the chamber including a flexible membrane operable to agitate contents in the chamber 15104 providing one or more fluidic valves coupled to the chamber, the one or more fluidic valves enabling a pump to control flow of one or more fluids through the chamber 151042 providing one or more channels disposed between at least one fluidic valve of the one or more fluidic valves and the chamber, at least one of the one or more channels configured to include a reagent bead 151044 enabling performance of the one or more staining procedures via controlling fluid flow into the chamber through at least one of the one or more fluidic valves, the at least one of the one or more fluidic valves coupled to a magnetic element responsive to a magnetic field generator in the auto-staining instrument, the magnetic element actuating the at least one of the one or more fluidic valves 151046 providing the one or more fluidic valves as peristaltic pumps and/or operable with one or more pumps associated with the auto-staining instrument 151047 providing within each of the one or more self-contained sample processing receptacles a magnetic element coupled to the flexible membrane, the magnetic element responsive to a magnetic field generator disposed within one or more of the auto-staining instrument and/or a module disposed within the auto-staining instrument, the magnetic element adapted to cause agitation of the chamber using the flexible membrane when the magnetic field generator is activated, the magnetic field generator adapted to produce one or more magnetic fields that apply force to the magnetic element, whereby the flexible membrane responds 15106 hermetically sealing at least one of the one or more self-contained sample processing receptacles 15108

AUTOMATIC SAMPLE STAINING SYSTEM

IN THE CROSS-REFERENCE TO RELATED APPLICATIONS

This application is a divisional of U.S. patent application Ser. No. 12/135,925, filed Jun. 9, 2008, and currently pending before the United States Patent and Trademark Office.

TECHNICAL FIELD

This invention relates generally to medical and laboratory equipment, and more specifically to one or more automated systems and methods for preparation, staining, and processing of cells and tissue preparations.

BACKGROUND

Medical and research laboratories study tissues and cells using a microscope. Researchers and medical professionals typically require a visual contrast between organelles within a cell, and between the cell and the extra-cellular matrix to study the tissues and cells. A special optical method such as a phase contrast can partially remedy this situation. A method of choice is to process specimen with a staining method such as applying dyes or colors to tissues to increase contrast. A widely used histological stain is hematoxylin and eosin (H&E). For example, cell nuclei can be stained black and/or blue in color by the hematoxylin component stains, and cell cytoplasm and most connective tissue fibers can be stained in various intensities and/or shades of red, pink, and/or orange by eosin stains. The contrasting method can reveal more than merely revealing the cell and organelles in tissue. Furthermore, with the use of antibodies and nucleic acid probes, it is also possible to detect some specific antigens and nucleic acid sequences giving information on the physiological condition of cell and tissues that can be use for medical diagnostic and research. The procedures to achieve these results are long and tedious and, as a result, expensive. Existing tissues stainers and immuno-stainers are large, expensive, and limited to few applications.

The reason for the expense is due in part to the need for tissue samples to be removed from a patient and processed by several organizations for histological examination. The characteristics of a tissue sample often provide important information regarding the health of an individual, but the characteristics are impossible to determine without assistance from multiple labs, personnel and diagnosticians due to the complexity required for staining the tissue samples.

The process typically begins by removing a tissue sample from a living organism, fixing the sample, embedding the fixed tissue in a material such as paraffin, and slicing the embedded fixed tissues into very thin sections. This procedure produces a histological specimen.

The histological specimens prepared according to either the paraffin-embedding method can be analyzed in a variety of ways, such as staining the sample to identify nucleic acids, or probing the sample with detectably-labeled antibodies.

Biological analysis using thin sections of embedded fixed tissue frequently applies to the diagnosis and prognosis of diseases and conditions such as cancer. For instance, a biopsy may be performed to determine whether a core or fragment of tissue removed from the patient is cancerous. Thus, a histological specimen is prepared from the tissue. The specimen is analyzed microscopically to determine whether the tissue exhibits the hallmarks of neoplasia or cancer.

It is known that tissue microarrays can be configured by combining hundreds of tissue samples in a single paraffin block to enable multiple tissue samples to be analyzed simultaneously. (Kononen, J, et al., Nature Medicine 4:767-768 (1998)). Thin sections from the tissue can later be analyzed using a variety of techniques, including DNA and RNA in situ hybridization and immunohistochemistry. (Bubendorf, L, et al., Cancer Res. 59:803-806 (1999)). Immunohistochemical markers or labels are often used in histology for identifying certain characteristics of a cell, for example, whether the cell is undergoing mitosis or expression of a certain antigen.

A known issue with the variety of techniques available to tissue samples is that many small labs and doctor's offices and hospitals lack the facilities to perform the analysis due to the complexity of the current techniques.

Typically, a doctor's office or laboratory can take biopsies and transfer them to laboratories for setting in paraffin or other fixative. After, tissues are set in a fixative however, transfer of the tissues to other specialized analysis locations takes place due to the complexity of preparing a slide for proper analysis. Fixed tissues can be stored within a vapor phase liquid nitrogen freezer system to maintain tissue. For example, deparafinization requires paraffin removal from the section of tissue with xylene. If the tissues are to be stained with an aqueous solution, then the slides must rehydrated in graded ethanol baths. Typically, the approach is to gently agitate the slides by repeated immersion ~20× in each bath including xylene for 2 minutes, 100% EtOH (×2), 95% EtOH (×1), 80% EtOH (×1), and H2O (×1).

One common stain for formalin fixed paraffin tissues is Hematoxylin and Eosin (H&E). Hematoxylin stains negatively charged nucleic acids blue. The eosin stains proteins pink. The hematoxylin or the eosin can also be used by themselves in more dilute form as counterstains for immunoperoxidase staining. Such staining requires dilution of the stain 1:4 with H2O or EtOH, respectively. Slides to be stained must be washed in ethanol, and then washed with Hematoxylin, 2 minutes (×1), Running water (×1), Acid alcohol (×1), H2O (×1), Ammonia solution (×1), Running water 5 minutes (×1), 80% EtOH (×1), Eosin 15 seconds, 95% EtOH (×2), 100% EtOH (×2).

A stain appropriate for auto-staining is the "Wright Giemsa" stain which requires heat fixation by warming a slide. Next, the slide can be exposed to alcohol, 30% to 80. The stain remains on the slide for 30 to 60 seconds, followed by a running water rinse, drying and covering with oil or slide adhesive.

Another stain used for slides includes a benzidine stain, that is a specialized stain configured to identify erythroid cells. To stain such a slide requires a methanol bath, 10-15 seconds followed by benzidine for 5 minutes, then peroxide, dionized water for 2.5 minutes, hematoxylin stain for 1.5 minutes, and a water rinse.

The above sampling of staining protocols and chemicals provides ample reason why such complex procedures are performed in specialized laboratories. Given the different protocols for preparing slides for stains, the toxic chemicals used such as benzidine, typical doctor's offices and local laboratories have limited resources for known auto-staining systems that are capable of a plurality of auto-stainings. Typically, such local operations will invest in simple stain auto-stain systems.

Accordingly there is a need for an efficient and reduced complexity system and method for tissue staining and analysis that enables laboratory analysis and staining of tissue samples.

SUMMARY

Embodiments herein provide a system and method for autostaining. In accordance with an embodiment, a method for staining of one or more samples includes but is not limited to providing one or more self-contained sample processing receptacles, each of the one or more self-contained sample processing receptacles configured to be inserted into an auto-staining instrument; and enabling one of one or more staining procedures appropriate for the one or more samples as a function of a choice of self-contained sample processing receptacle, each of the one or more self-contained sample processing receptacles configured to process each inserted sample of the one or more samples within the self-contained sample processing receptacle. In addition to the foregoing, other method aspects are described in the claims, drawings, and text forming a part of the present application.

In another aspect, a computer program product comprising a computer readable medium configured to perform one or more acts for staining a sample includes but is not limited to a signal bearing medium bearing at least one of one or more instructions for enabling one of one or more staining procedures appropriate for one or more samples as a function of a choice of one or more self-contained sample processing receptacles, each of the one or more self-contained sample processing receptacles configured to process each inserted sample of the one or more samples within the self-contained sample processing receptacle; one or more instructions for receiving first identification data from a sample contained in one of the one or more self-contained sample processing receptacles; one or more instructions for receiving staining procedure data from the self-contained sample processing receptacle; and one or more instructions for comparing the first identification data from the sample and the staining procedure data from the self-contained sample processing receptacle to confirm that the choice of self-contained sample processing receptacle is valid. In addition to the foregoing, other computer program product aspects are described in the claims, drawings, and text forming a part of the present application.

In another aspect, a system for automatic staining of one or more biological samples, includes a processor; a memory coupled to the processor, the memory configured to include a plurality of one or more sample processing procedures; and a sample processing component operably coupled to the processor, the sample processing component configured to receive a first self-contained sample processing receptacle, the first self-contained sample processing receptacle configured to hold at least one of the one or more biological samples, and the first self-contained sample processing receptacle configured to include a computer-readable identification indicating one of the plurality of one or more sample processing procedures to enable the sample processing component to compare the indicated one of the plurality of one or more sample processing procedures associated with each self-contained sample processing receptacle with a second computer-readable identification of an inserted sample.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject described herein will become apparent in the text set forth herein.

BRIEF DESCRIPTION OF THE DRAWINGS

A better understanding of the subject matter of the present application can be obtained when the following detailed description of the disclosed embodiments is considered in conjunction with the following drawings, in which:

FIG. 3 is a diagram illustrating different views of an auto-staining instrument in accordance with an embodiment of the present invention.

FIG. 7 is a schematic diagram illustrating data ports and memory mediums in accordance with an embodiment of the present invention.

FIG. 14 is a cross-sectional view of an auto-staining module is depicted, according to various embodiments.

DETAILED DESCRIPTION

Figure 1:
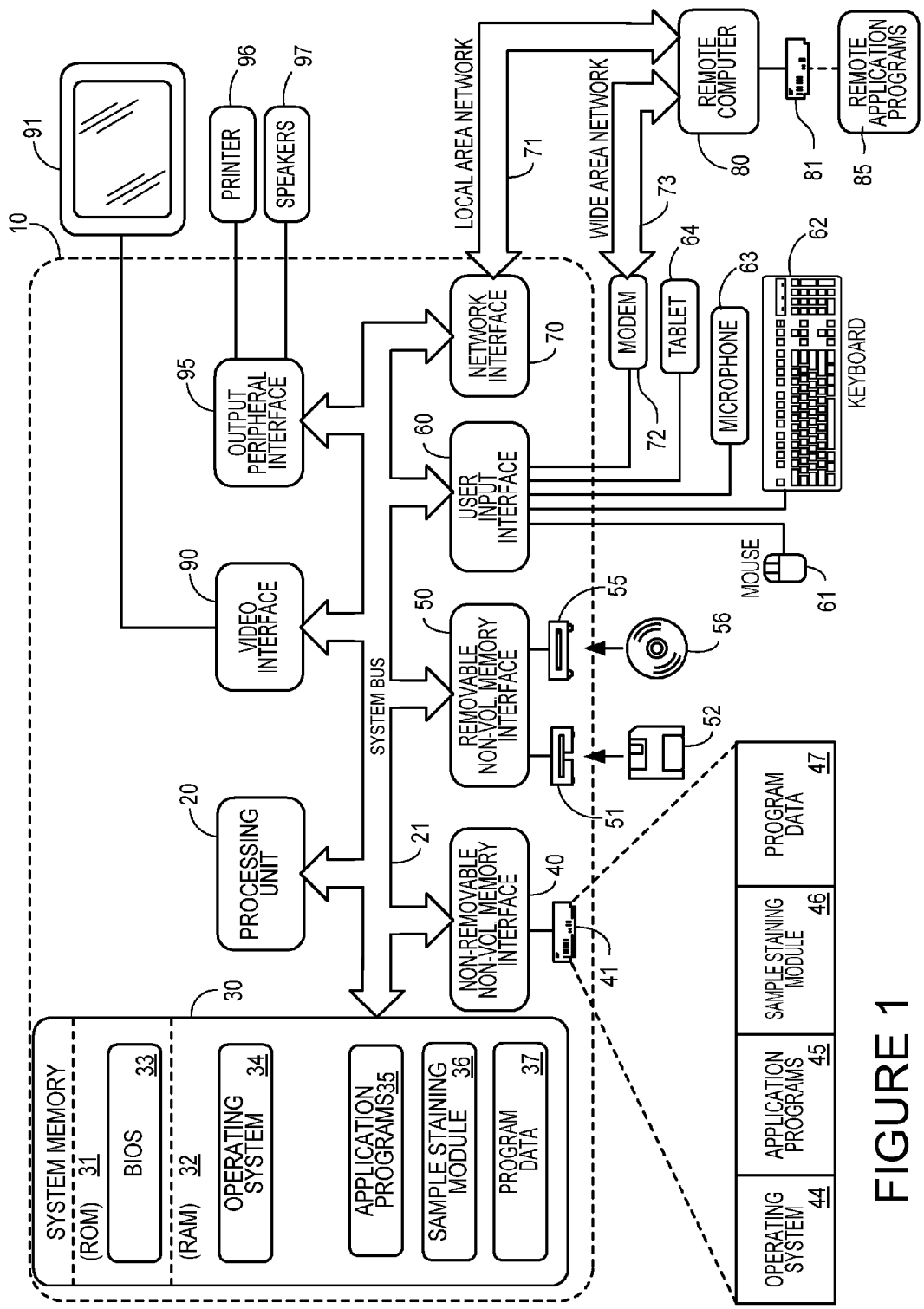
FIG. 1 is a block diagram of an exemplary computer architecture that supports the claimed subject matter.

Those with skill in the computing arts will recognize that the disclosed embodiments have relevance to a wide variety of applications and architectures in addition to those described below. In addition, the functionality of the subject matter of the present application can be implemented with the assistance of software, hardware, or a combination of software and hardware. The software portion can be stored in a memory or recording medium and executed by a suitable instruction execution system such as a microprocessor.

Embodiments herein relate to apparatuses, methods and/or systems for auto-staining of slides for medical purposes. Certain embodiments disclosed herein can be performed with the use of a computer and software. By way of example, and with reference to FIG. 1, an exemplary computing system for implementing the embodiments includes a general purpose computing device in the form of a computer 10. Components of the computer 10 can include, but are not limited to, a processing unit 20, a system memory 30, and a system bus 21 that couples various system components including the system memory to the processing unit 20. The system bus 21 can be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 10 typically includes a variety of computer readable media. Computer readable media can be any available media that can be accessed by the computer 10 and includes both volatile and nonvolatile media, and removable and non-removable media. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital video disks (DVD) or other optical disk storage, magnetic cassettes, magnetic tape, magnetic disk storage or other magnetic storage devices, or any other medium which can be used to store the desired information and which can be accessed by the computer 10. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 30 can include computer storage media in the form of volatile and/or nonvolatile memory such as read only memory (ROM) 31 and random access memory (RAM) 32. A basic input/output system 33 (BIOS), including the basic routines that help to transfer information between elements within computer 10, such as during start-up, is typically stored in ROM 31. RAM 32 typically contains data and/or program modules that are immediately accessible to and/or presently being operated on by processing unit 20. By way of example, and not limitation, FIG. 1 illustrates operating system 34, application programs 35, other program modules 36 and program data 37. FIG. 1 is shown with program modules 36 including an image processing module in accordance with an embodiment as described herein.

The computer 10 can also include other removable/non-removable, volatile/nonvolatile computer storage media. By way of example only, FIG. 1 illustrates a hard disk drive 41 that reads from or writes to non-removable, nonvolatile magnetic media, a magnetic disk drive 51 that reads from or writes to a removable, nonvolatile magnetic disk 52, and an optical disk drive 55 that reads from or writes to a removable, nonvolatile optical disk 56 such as a CD ROM, DVD ROM, and/or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 41 is typically connected to the system bus 21 through a non-removable memory interface such as interface 40, and magnetic disk drive 51 and optical disk drive 55 are typically connected to the system bus 21 by a removable memory interface, such as interface 50. An interface for purposes of this disclosure can mean a location on a device for inserting a drive such as hard disk drive 41 in a secured fashion, or a in a more unsecured fashion, such as interface 50. In either case, an interface includes a location for electronically attaching additional parts to the computer 10.

The drives and their associated computer storage media, discussed above and illustrated in FIG. 1, provide storage of computer readable instructions, data structures, program modules and other data for the computer 10. In FIG. 1, for example, hard disk drive 41 is illustrated as storing operating system 44, application programs 45, other program modules, including specimen processing module 46 and program data 47. Program modules 46 is shown including an specimen processing module, which can be configured as either located in modules 36 or 46, or both locations, as one with skill in the art will appreciate. More specifically, specimen processing modules 36 and 46 could be in non-volatile memory in some embodiments wherein one or more specimen processing modules run automatically in an environment. In other embodiments, specimen processing modules could be part of an embedded system. Note that these components can either be the same as or different from operating system 34, application programs 35, other program modules, including specimen processing module 36, and program data 37. Operating system 44, application programs 45, other program modules, including specimen processing module 46, and program data 47 are given different numbers hereto illustrate that, at a minimum, they are different copies. In one embodiment, a user can enter commands and information into the computer 10 through input devices such as a tablet, or electronic digitizer, 64, a microphone 63, a keyboard 62 and pointing device 61, commonly referred to as a mouse, trackball or touch pad. Other input devices (not shown) can include a satellite dish, scanner, or the like. These and other input devices can be connected to the processing unit 20 through a user input interface 60 that is coupled to the system bus, but can be connected by other interface and bus structures, such as a parallel port or a universal serial bus (USB). A monitor 91 or other type of display device can be connected to the system bus 21 via an interface, such as a video interface 90. The monitor 91 can also be integrated with a touch-screen panel or the like. Note that the monitor and/or touch screen panel can be physically coupled to a housing in which the computing device 10 is incorporated, such as in a tablet-type personal computer. In addition, computers such as the computing device 10 can also include other peripheral output devices such as speakers 97 and printer 96, which can be connected through an output peripheral interface 95 or the like.

The computer 10 can operate in a networked environment using logical connections to one or more remote computers, which could be other cell phones with a processor or other computers, such as a remote computer 80. The remote computer 80 can be a personal computer, a server, a router, a network PC, PDA, cell phone, a peer device or other common network node, and typically includes many or all of the elements described above relative to the computer 10, although only a memory storage device 81 has been illustrated in FIG. 1. The logical connections depicted in FIG. 1 include a local area network (LAN) 71 and a wide area network (WAN) 73, but can also include other networks. Such networking environments are commonplace in offices, enterprise-wide computer networks, intranets and the Internet. For example, in the subject matter of the present application, the computer system 10 can comprise the source machine from which data is being migrated, and the remote computer 80 can comprise the destination machine. Note however that source and destination machines need not be connected by a network or any other means, but instead, data can be migrated via any media capable of being written by the source platform and read by the destination platform or platforms.

When used in a LAN or WLAN networking environment, the computer 10 is connected to the LAN through a network interface or adapter 70. When used in a WAN networking environment, the computer 10 typically includes a modem 72 or other means for establishing communications over the WAN 73, such as the Internet. The modem 72, which can be internal or external, can be connected to the system bus 21 via the user input interface 60 or other appropriate mechanism. In a networked environment, program modules depicted relative to the computer 10, or portions thereof, can be stored in the remote memory storage device. By way of example, and not limitation, FIG. 1 illustrates remote application programs 85 as residing on memory device 81. It will be appreciated that the network connections shown are exemplary and other means of establishing a communications link between the computers can be used.

Figure 2:
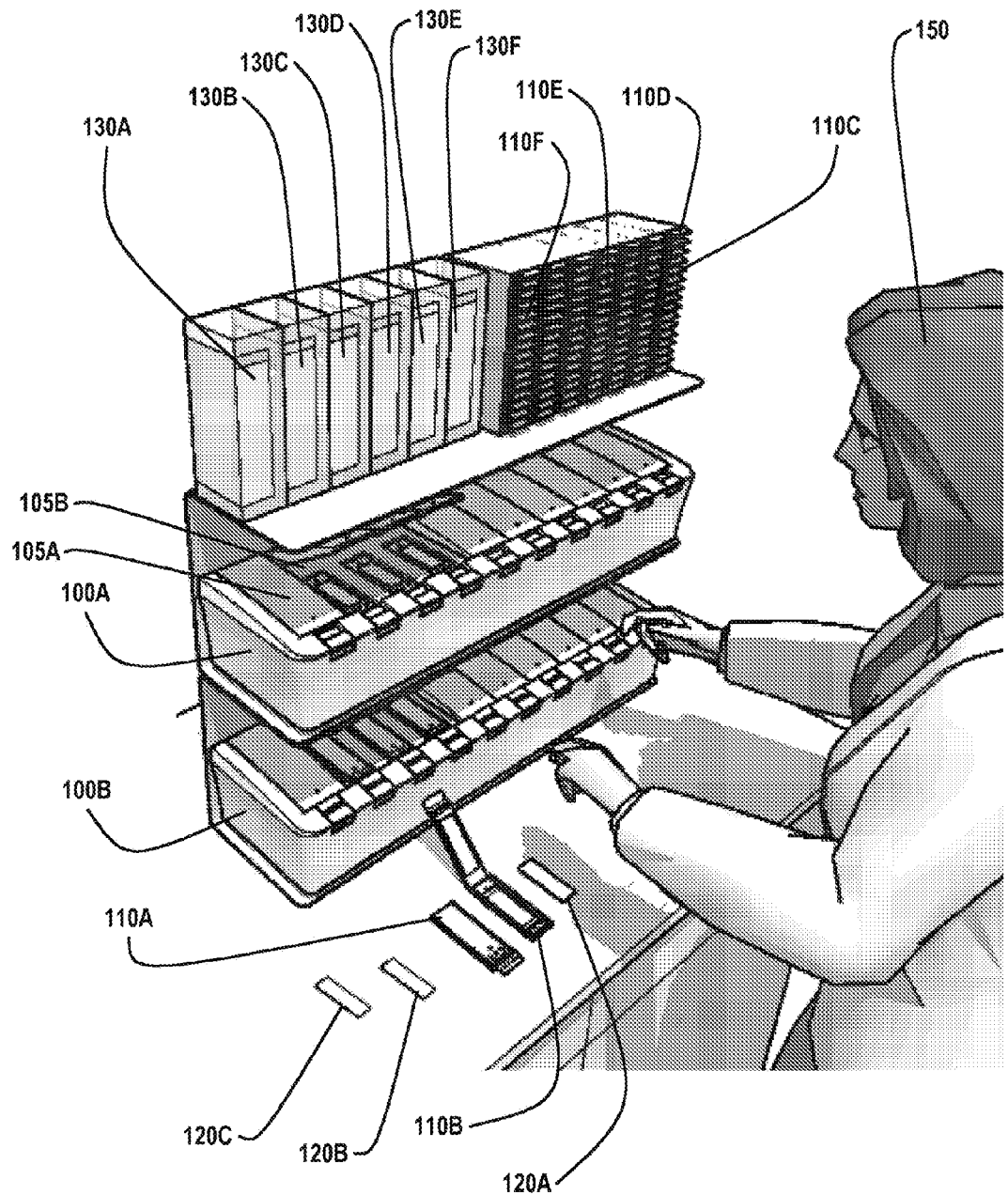
FIG. 2 is a diagram of an operator using a self-contained sample processing receptacle, module and auto-staining instrument in accordance with an embodiment.

Referring now to FIG. 2, a system for enabling efficient and local auto-staining functionality is depicted in accordance with various embodiments. "Auto-staining" as used herein refers to methods and/or systems that enable automated staining of tissues on slides. More particularly, "auto-staining" herein includes staining to enable biological analysis of thin sections of embedded fixed tissue or other matter, for example for diagnosis and prognosis of diseases and conditions such as cancer. Thus, a histological specimen can be analyzed microscopically after "auto-staining".

Tissue microarrays can be configured by combining hundreds of tissue samples in a single paraffin block to enable multiple tissue samples to be analyzed simultaneously. Embodiments herein also enable "auto-staining" for a nucleic acid (DNA/RNA) microarray. A nucleic acid microarray is a support, which can be a slide. Laboratories detect sequences by hybridization using nucleic acid microarrays. Typically, a slide will contain dots of synthesized or tissue extracted nucleic acid.

Embodiments herein further enable "auto-staining" of protein/peptide microarrays in which peptides are extracted from tissues and are then are fixed on a slide for subsequent detection by antibodies.

More specifically, the auto-stainer system in accordance with embodiments herein includes methods and systems for labeling and staining tissue specimens that are attached to slides. Additionally, the labeling and staining methods and systems apply to other types of labeling and samples. For example, other types of sample staining include but are not limited to, fluorescent applications such as FISH (fluorescent in situ hybridization), nucleic acid microarray hybridization, and protein microarray labeling.

In a nucleic acid microarray hybridization protocol, a nucleic acid (DNA, RNA or chemically analogous molecules) are extracted from biological material or synthesized. The nucleic acid extract is fixed onto a support such as a glass slide and the resulting support is processed for hybridization using various labeled nucleic acid or analog probes.

The nucleic acid probes can then be detected using various fluorochromes. (Using an enzymatic colorimetric method instead or even a radioactive tracers would be a conceptually trivial implementation.)

In a protein microarray protocol, dots of proteins extracted from tissues are fixed into a slide and processed by methods very similar to immunohistochemistry ("IHC") for the detection of protein antigen.

As shown, the system can include one or more auto-staining instruments 100A and/or 100B. Each of auto-staining instruments 100A and/or 100B can include one or more auto-staining modules 105A and/or 105B, and each auto-staining module 105A/105B is configured to receive one of self-contained sample processing receptacles 110A-110F. Each of the one or more self-contained sample processing receptacles 110A-110F is configured to receive a tissue sample in need of staining, processing or the like, such as a tissue on one of slides 120A-120C.

Each of self-contained sample processing receptacles 110A-110F are configured as sealable chambers to enable processing therein independent from other self-contained sample processing receptacles in a same auto-staining instrument 100A/100B. For example, a single auto-staining instrument 100A can apply different staining protocols to each different self-contained sample processing receptacle 110A-110F as are present in the auto-staining instrument 110A, limited only by the availability of reagents either on board or disposed within each self-contained sample processing receptacle 110A/110B. Each self-contained sample processing receptacle 110A/110B can apply reagents present in-situ and/or reagents supplied by the auto-staining instrument as required by a given staining protocol. According to an embodiment, the staining protocol can be determined by operator 150 when determining which self-contained sample processing receptacle 110A/110B is appropriate for a staining protocol.

FIG. 2 further illustrates an operator 150. As described, according to an embodiment, operator 150 can determine which staining protocol to apply to any given tissue by choosing an appropriate self-contained sample processing receptacle 110A-110F. For example, one or more self-contained sample processing receptacles can be configured as including one or more reagents, such as beads or the like, within the self-contained sample processing receptacles 110A/110B. The beads can be predetermined to be appropriate for one or more specific type of staining protocol. Alternatively or in addition to in-situ reagent beads, reagents can be supplied via a fluidic system incorporated into auto-staining instrument 100A in one or more of containers 130A-130F. Additionally, the self-contained sample processing receptacles 110A/110B can be configured as requiring additional reagent via auto-staining instrument 100A/110B. Also, in one embodiment, self-contained sample processing receptacle 110A/110B could include a partial-reagent bead requiring additional chemicals via receptacles 130A-130F, or the like. In each case, however, the processing takes place within a sealed chamber of the self-contained sample processing receptacle 110A/110B.

As shown in FIG. 2, operator 150 can place slide 120A into self-contained sample processing receptacle 110B and can place self-contained sample processing receptacle 110B into auto-staining module 105B of auto-staining instrument 100A. In some embodiments, self-contained sample processing receptacle 110B can be placed into auto-staining module 105B while auto-staining is being performed in auto-staining module 105A on a different self-contained sample processing receptacle 110A within same auto-staining instrument 110A. Moreover, a first auto-staining can be performed in auto-staining module 105A while a different second auto-staining can be performed in any different auto-staining module, such as auto-staining module 105B. For example, a portion of a first auto-staining procedure can be performed using auto-staining module 110A while a portion of a second auto-staining procedure is performed using auto-staining module 110B. For instance, the portion of the first auto-staining procedure and the portion of the second auto-staining procedure can be performed in a concurrent fashion. In some embodiments, the first auto-staining procedure and the second auto-staining procedure can be the same or different. More particularly, as one of skill in the art will appreciate, staining of tissue samples can be a long process requiring heating, cooling, applying stain, rinsing of reagent and the like. Depending on the protocol required for a particular staining event, the length of time required (according to some measure of some metric) within each self-contained sample processing receptacle can be different. Thus, according to an embodiment, rather than requiring a largest common denominator of time to determine how many staining protocols can be performed, each self-contained sample processing receptacle is configured to be independent from other self-contained sample processing receptacles even within the same auto-staining instrument 100A/100B.

In various embodiments, one or more reservoirs 130A-130F can be coupled to one or more auto-staining instruments 100A and/or 100B. For example, reservoirs 130A-130F can be used as vessels or reservoirs for reagents, buffers, liquids, semi-liquids, gases, wastes and/or other fluids. In various embodiments, a reagent can include antibodies, molecular probes, alcohols, dyes, and/or enzymes, among others.

In one example, auto-staining instruments 100A and 100B can share contents of each of reservoirs 130A-130F via a sharing system. In one instance, auto-staining instrument 100A and auto-staining instrument 100B can be separately coupled to one or more of reservoirs 130A-130F. In another instance, auto-staining instrument 100B can be coupled to one or more of reservoirs 130A-130F through auto-staining instrument 100A. In various embodiments, auto-staining instruments 100A/100B can be "daisy chained" together to access one or more of reservoirs 130A-130F. For example, a first auto-staining instrument can be coupled to one or more of reservoirs 130A-130F, a second auto-staining instrument can be coupled to the first auto-staining instrument, and a third auto-staining instrument can be coupled to the second auto-staining instrument. The second auto-staining instrument can access one or more of reservoirs 130A-130F through the first auto-staining instrument, and the third auto-staining instrument can access one or more of reservoirs 130A-130F through the second auto-staining instrument.

Turning now to FIG. 3, Auto-staining instruments 100A and 100B are depicted, according to various embodiments. As shown, auto-staining instrument 100A can include auto-staining modules 105A-105J, and auto-staining instrument 100B can include auto-staining modules 105K-105T.

Figure 4:
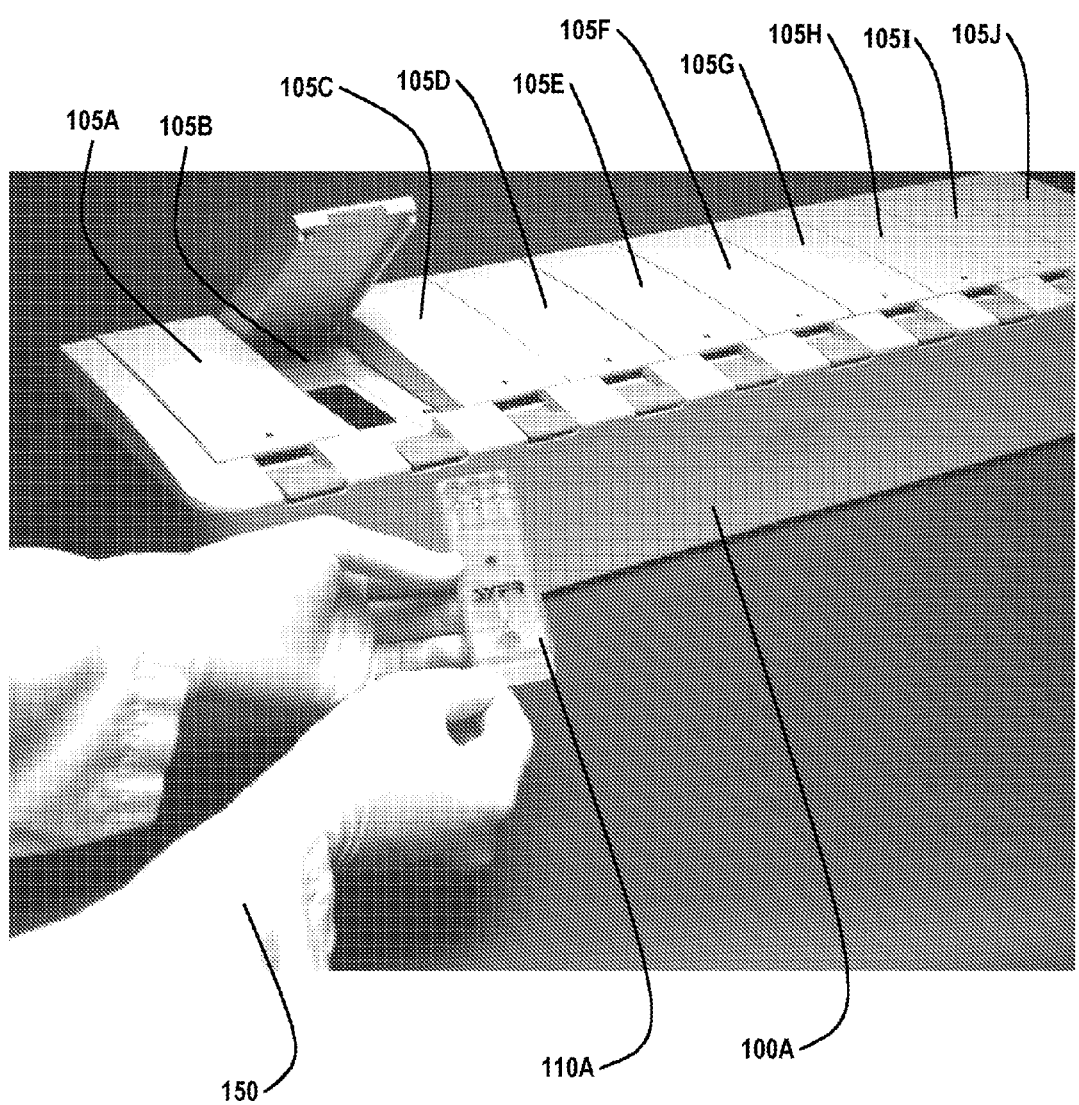
FIG. 4 is a diagram illustrating a self-contained sample processing receptacle and auto-staining instrument with modules in accordance with an embodiment of the present invention.
Figure 5:
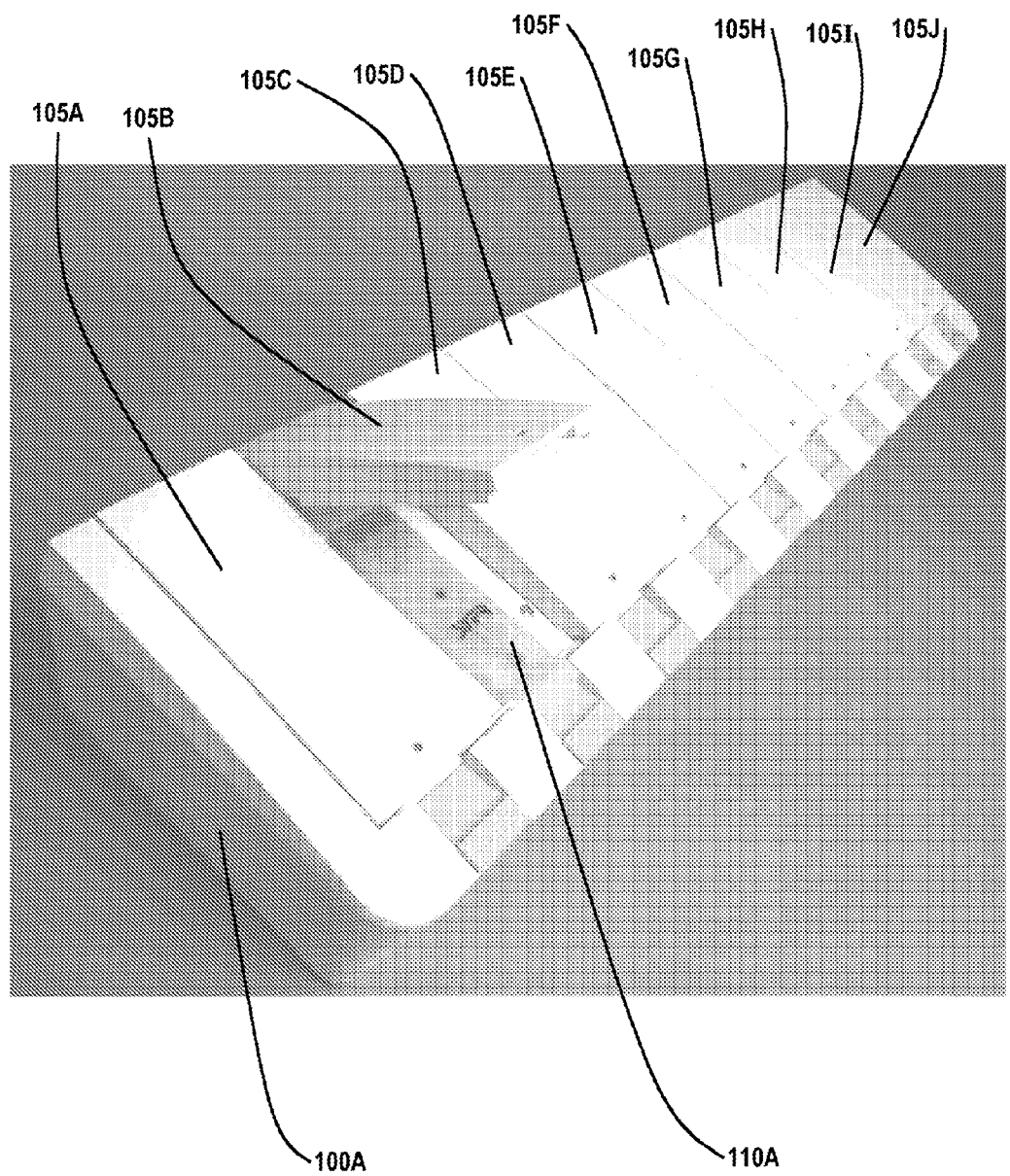
FIG. 5 is a diagram illustrating a self-contained sample processing receptacle inserted into an auto-staining instrument with modules in accordance with an embodiment of the present invention.

Referring now to FIGS. 4 and 5, auto-staining instrument 100A is depicted, according to various embodiments. As shown in FIG. 4, operator 150 can place self-contained sample processing receptacle 110A into auto-staining module 105B. As illustrated, auto-staining module 105B has its door in an open position. FIG. 5 shows self-contained sample processing receptacle 110A in auto-staining module 105B.

Figure 6:
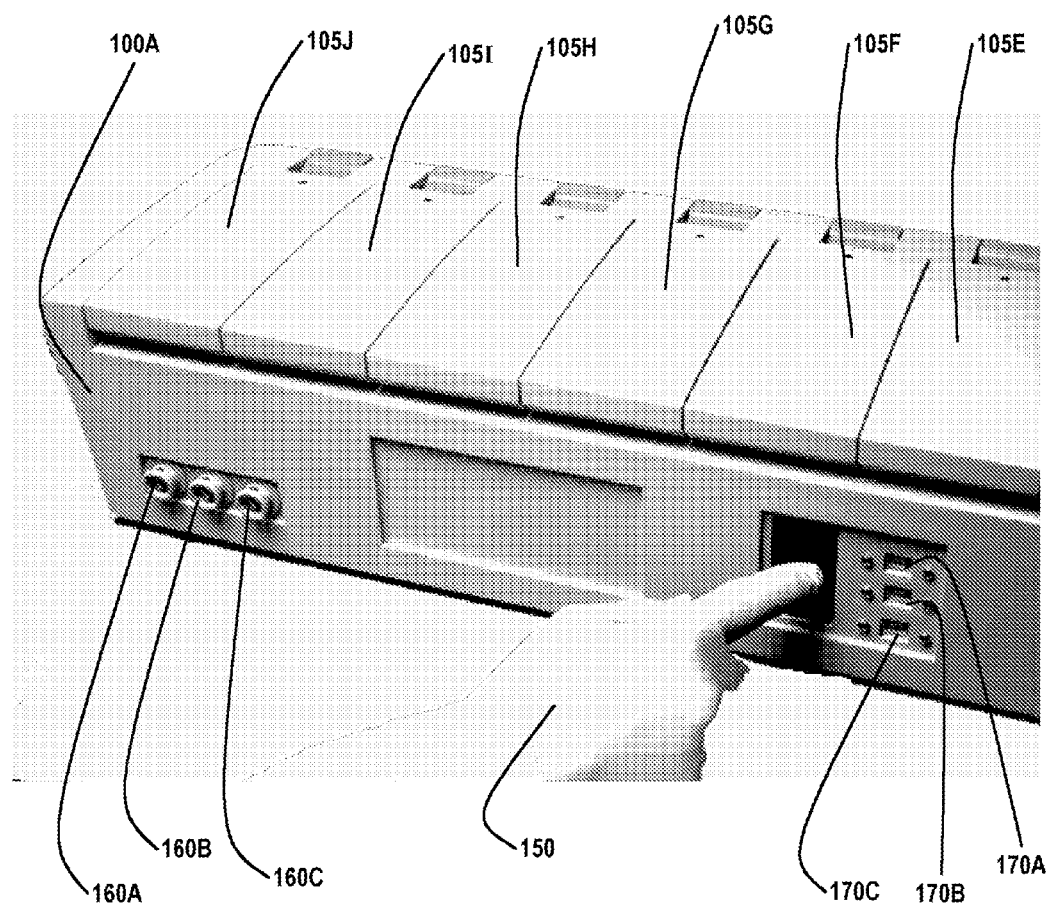
FIG. 6 is a diagram illustrating a back side of an auto-staining instrument with modules in accordance with an embodiment of the present invention.

Referring now to FIG. 6, a portion of an auto-staining instrument is depicted according to various embodiments. As illustrated, in some embodiments, auto-staining instrument 100A can include one or more fluidic ports or connectors 160A-160C that can be used in connecting auto-staining instrument 100A to various reservoirs, such as reservoirs 130A-130F. For example, fluidic connector 160A can be coupled to a selection valve that can select among reservoirs 130A-130D. Reservoirs 130A-130D can also be used for reagents, buffers, liquids, and/or other fluids. Fluidic connector 160B can be coupled to reservoir 130E that can be used for water, and fluidic connector 160C can be coupled to reservoir 130F that can be used for waste.

In one or more embodiments, reservoirs could be used to store some fluids. For example, a fluidic connector can be coupled to a water supply. For instance, a laboratory can have a distilled or de-ionized water supply that can be coupled to fluidic connector 160B. In another instance, the laboratory can have a waste system that can be coupled to fluidic connector 160C.

As illustrated, auto-staining instrument 100A can include one or more data ports 170A-170C. In various embodiments, one or more data ports can transmit and/or receive data with various systems, subsystems, networks, and/or devices, and data can be transferred through, to, and from various mediums. For example, auto-staining instrument 100A can use data port 170A in communicating data via Ethernet, universal serial bus (USB), RS-232 signaling, RS-485 signaling, IEEE 1394 (e.g., FireWire), optical fiber, DSL, a public switched telephone network (PSTN), ISDN, general purpose IO (GPIO), IEEE 1284, IEEE 488 (e.g., GPIB), MIDI signaling, I$^2$C (Inter-Integrated Circuit), SCSI, SPI (serial peripheral interface), TWI (two-wire interface), MICROWIRE, and/or 1-Wire, among others.

In some embodiments, an auto-staining instrument can communicate data in a wireless fashion. For example, auto-staining instrument 100A can use data port 170A to communicate data in a wireless fashion. In some embodiments, wireless communication can be accomplished using various wireless technologies. For example, these wireless technologies can include using various frequencies (e.g., 330 Mhz, 900 MHz, 1.7 GHz, 2.4 GHz, 3.6 GHz, 5 GHz, etc.), various encoding techniques (e.g., spread spectrum, code division multiple access, time division multiple access, frequency division multiple access, etc.), IEEE 802.11, IEEE 802.16, IEEE 802.15, satellite communications, GPRS (general packet radio service), infrared serial communications, optical communications, among others.

In some embodiments, communicating data can include using one or more security systems and/or methods. For example, data can be communicated using a virtual private network (VPN), IPSec, and/or cryptography, among others. In various embodiments, communicating data can include using one or more authentication systems and/or methods. For example, data can be communicated using one or more digital certificates (e.g., X.509 certificates), CRCs (cyclic redundancy checks), MD5 hashes, SHA-160 hashes, among others. In some embodiments, communicating data using one or more authentication systems and/or methods can include using additional data. For example, first data can be for transport from one point to one or more other points. Second data (e.g., a shared secret) can be added to and/or combined with the first data to produce a first hash value. The first data and the first hash value can be received by one of the one or more other points. For instance, the one of the one or more other points can use the first data and the second data to produce a second hash value. If the first hash value and the second hash value match, the first data can be considered authenticated. Authentication failures can discard various data and/or produce one or more alerts. In various embodiments, the second data can include one or more memory mediums of the one or more other points.

Referring now to FIG. 7, various auto-staining instruments are depicted, according to one or more embodiments. As shown, auto-staining instruments 100A-100C can include various data ports and/or fluidic ports. Auto-staining instrument 100A can include fluidic ports or connectors 160A-160C and/or data ports 170A-170C, auto-staining instrument 100B can also include fluidic ports or connectors 160D-160F and/or data ports 170D-170F, and an auto-staining instrument 100C can include fluidic ports or connectors 160G-160I and/or data ports 170G-170I.

Additionally, according to an embodiment, auto-staining instruments 100A-100C can, respectively, include: a processor 175A coupled to a memory medium 177A; a processor 175B coupled to a memory medium 177B; and a processor 175C coupled to a memory medium 177C. As shown, processor 175A can be coupled to data ports 170A-170C, processor 175B can be coupled to data ports 170D-170F, and processor 175C can be coupled to data ports 170G-170I.

In some embodiments, a processor (e.g., one of processors 175A-175C) can be configured to execute instruction from a memory medium (e.g., e.g., one of memory mediums 177A-177B) and/or from an input/output (I/O) system (e.g., through one or more data ports 170A-170C, among others). For example, the processor can be or include a microprocessor and/or a microcontroller configured to implement a given instruction set architecture (ISA). For instance, the given ISA can include portions of or all of one or more of a PowerPC ISA, an Intel x86 ISA, a MIPS ISA, an ARM ISA, a SPARC ISA, a Propeller ISA, an AVR 8-bit RISC ISA, an AVR32 ISA, a JAVA ISA, and/or a Microchip PIC ISA, among others. In some embodiments, the processor can be or include one or more digital signal processors. In general, the terms "computer", "computing device", and "computer system" can be broadly defined to include any device having a processor that executes instructions from a memory medium.

In various embodiments, the memory medium can be configured to store data used in operating various systems and/or subsystems described herein. In some embodiments, the memory medium can be configured to store program instructions executable by a processor to implement various methods and/or systems described herein. In some embodiments, the memory medium can include various of memory technologies such as dynamic random access memory (DRAM), static random access memory (SRAM), non-volatile random access memory (NVRAM) (e.g., "flash" random access memory), EEPROM, EPROM, read-only memory (ROM), CDROM, CD-RW, DVDROM, DVD-RW, floppy disk, flash card, thumb drive, hard disk, RAID, network area storage (NAS), and/or storage area network (SAN), among others. All or one or more portions of the memory medium can be removable, and possibly, configured to be carried by a user. In some embodiments, the memory medium can include a combination and/or various combinations of storage technologies, as well as other storage technologies not specifically mentioned. In various embodiments, the memory medium can store various information and/or data structures that include information used in the system(s) and/or method(s) described herein.

For example, one or more data structures stored in the memory medium can include information associated with two or more auto-staining procedures. For instance, various identifications (e.g., identifications from various self-contained sample processing receptacles) can be associated with one or more auto-staining procedures stored in a data structure. Moreover, in some embodiments, various identification information can be used to index into the data structure stored in the memory medium.

Figure 8:
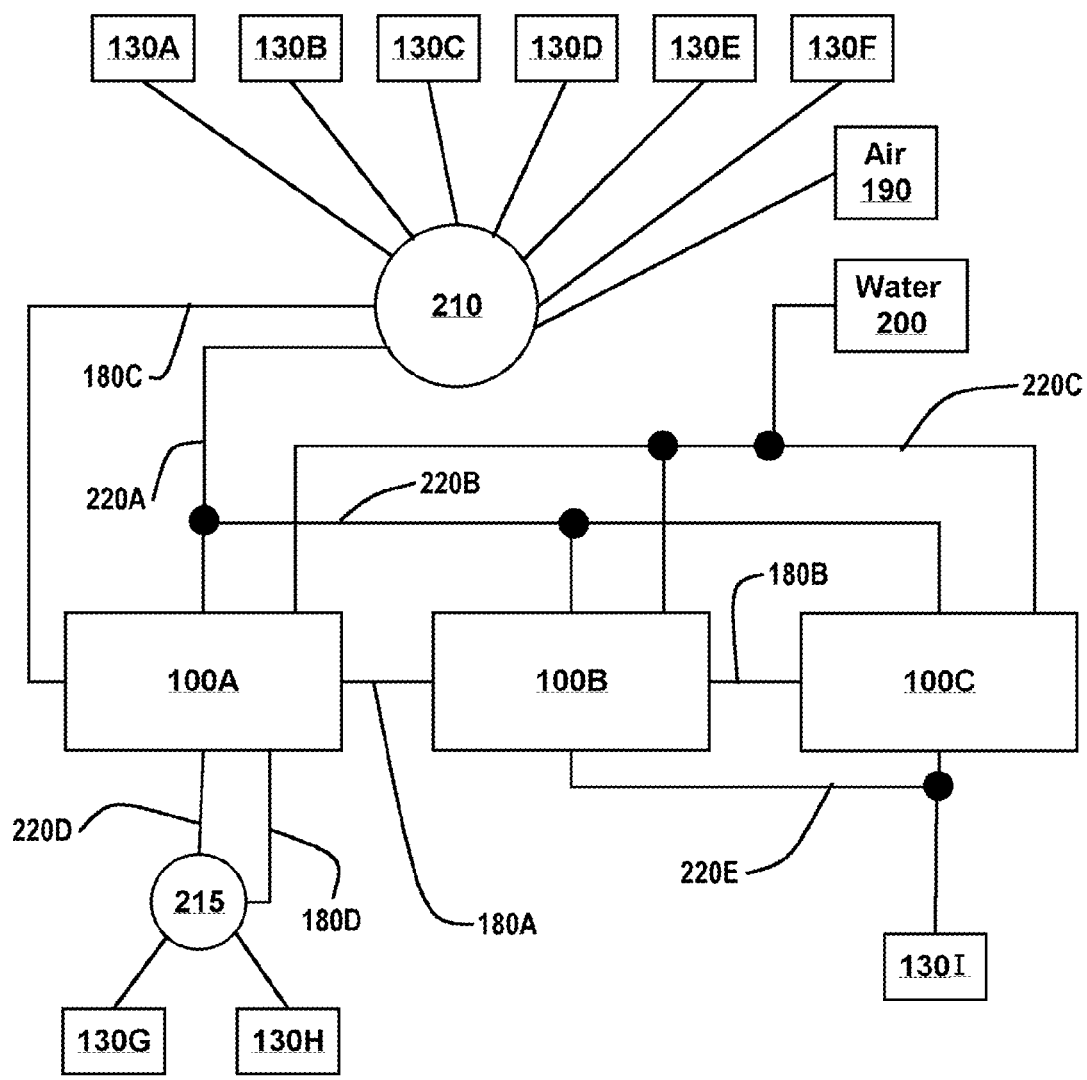
FIG. 8 is a schematic block diagram of auto-staining instruments 100A-100C and data ports in accordance with an embodiment of the present invention.

Referring now to FIG. 8, a block diagram is illustrated, according to various embodiments. As shown, auto-staining instrument 100A can be coupled to auto-staining instrument 100B through a data coupling 180A, and auto-staining instrument 100B can be coupled to auto-staining instrument through a data coupling 180B. For example, data ports 170A and 170D can be used to couple auto-staining instruments 100A and 100B, and data ports 170E and 170G can be used to couple auto-staining instruments 100B and 100C. In some embodiments, data port 170D can be used to couple auto-staining instruments 100A and 100B and can be used to couple auto-staining instruments 100B and 100C. Alternatively, separate data ports could be configured to couple two or more devices. In various embodiments, auto-staining instrument 100A can be coupled to a fluidic selection device 210 through a data coupling 180C. In various embodiments, fluidic selection device 210 can receive selection information via data coupling 180C, and the selection information can be associated with a reservoir, reagent, and/or a fluid selection.

In some embodiments, reservoirs 130A-130F and an air supply 190 can be coupled to fluidic selection device 210, and fluidic selection device 210 can be coupled to instrument auto-staining devices 100A-100C through a fluidic coupling 220A. For example, fluidic coupling 220A can include one or more tubings, pipes, conduits, etc. As shown, fluidic coupling 220A can be used to distribute one or more fluids from fluidic selection device 210. In one instance, fluidic coupling 220B can be coupled to one or more of fluidic connector or port 160A of auto-staining instrument 100A, fluidic connector or port 160D of auto-staining instrument 100B, and/or fluidic connector or port 160G of auto-staining instrument 100C. In another instance, a fluidic coupling 220C can be coupled to a water supply 200 and one or more of fluidic connector or port 160B of auto-staining instrument 100A, fluidic connector or port 160E of auto-staining instrument 100B, and/or fluidic connector or port 160H of auto-staining instrument 100C. In this fashion, auto-staining instruments 100A-100C can be "daisy chained" together, in some embodiments.

In various embodiments, auto-staining instrument 100A can be coupled to a waste selection device 215 via a fluidic coupling 220D, and waste selection device 215 can be coupled to reservoirs 130G and 130H. In some embodiments, different waste reservoirs can be used to handle different types of waste. For example, reservoir 130G can handle general waste from various auto-staining procedures, and reservoir 130H can handle waste from auto-staining procedures that can involve radioactive materials. Thus, reservoir 130H can be configured to receive and store radioactive waste. For instance, reservoir 130H can be lined with lead and/or other material(s). In another example, different reagents may not be able to be safely combined. Accordingly, these non-safely-combinable reagents can be stored in separate waste reservoirs when they are done being used. In various embodiments, other reservoirs can be used for other types of waste and can be configured, accordingly, to safely and/or appropriately handle such waste. In some embodiments, auto-staining instrument 100A can be coupled to waste selection device 215 through a data coupling 180D, where an auto-staining procedure can use data coupling 180D to switch waste selection device 215 between reservoirs 130G or 130H.

In some embodiments, auto-staining instruments 100B and 100C can be coupled to reservoir 130I via a fluidic coupling 220E. For example, reservoir 130I can be used to handle and/or store waste from various auto-staining procedures.

Figure 9:
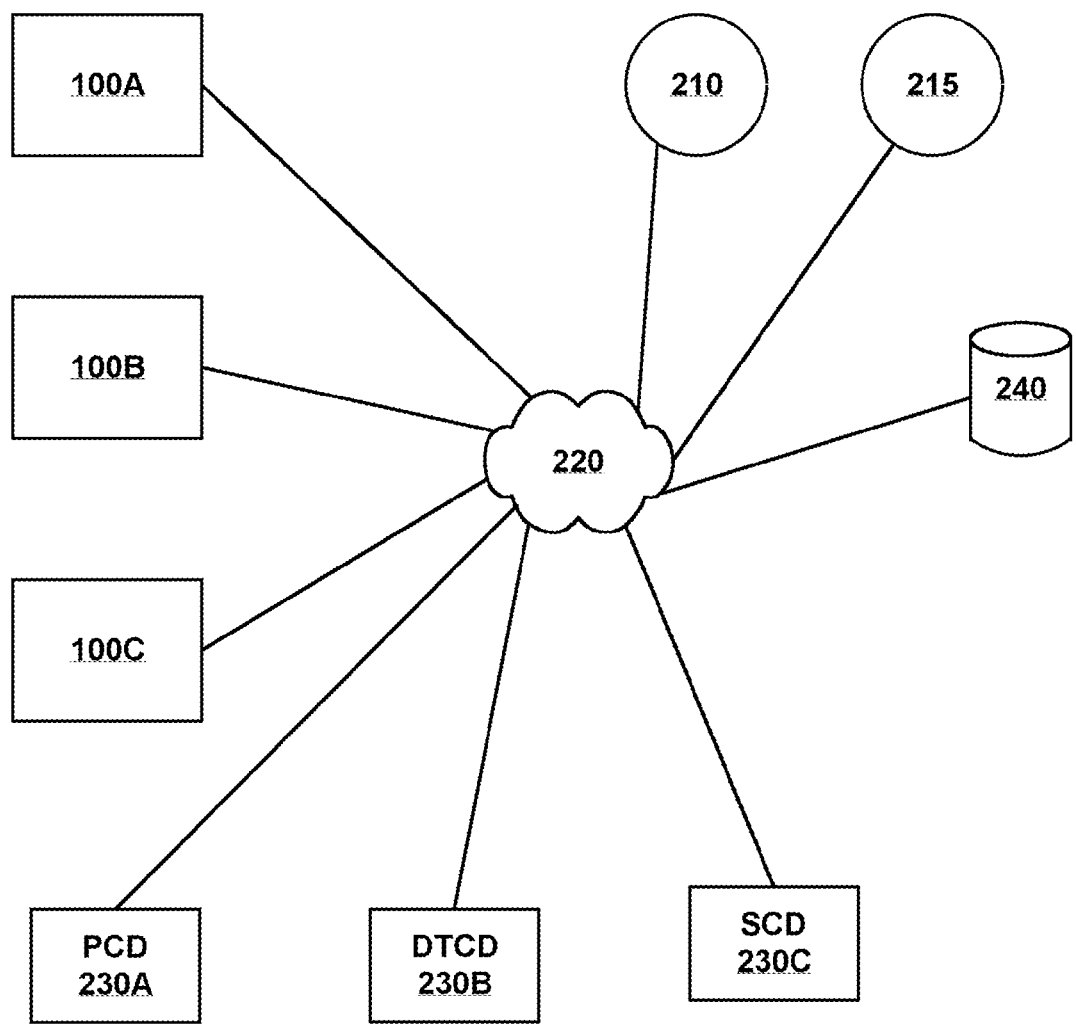
FIG. 9 is a schematic block diagram of auto-staining instruments 100A-100C and data port and database in accordance with an embodiment of the present invention.

Turning now to FIG. 9, a block diagram is illustrated in accordance with an embodiment. As shown, one or more of auto-staining instruments 100A-100C, waste selection device 215, fluidic selection device 210, a database 240, a portable computing device (PCD) 230A (e.g., a laptop, a personal digital assistant (PDA), a smart phone, etc.), a desk top computing device (DTCD) 230B, a server computing device (SCD) 230C, and/or a database 240 can be coupled to network 220. In some embodiments, each of auto-staining instruments 100A-100C, waste selection device 215, fluidic selection device 210, database 240, PCD 230A, DTCD 230B, SCD 230C and/or database 240 can communicate with network 220 over a wired or wireless connection. Network 220 can include a wireless network, a wired network, or a combination of wireless and wired networks. In various embodiments, network 220 can include and/or be coupled to various networks, such as a public switch telephone network (PSTN), a wireless telephone network (e.g., paging, cellular, satellite, etc.), an Internet, one or more local area networks (LANs), and/or wide area networks (WANs), among others.

In an alternative embodiment, one or more of auto-staining instruments 100A-100C, waste selection device 215, fluidic selection device 210, database 240, PCD 230A, DTCD 230B, SCD 230C, database 240, and/or network 220 can be used to implement at least a portion of any system and/or method described herein. In one example, network 220 can include one or more of data couplings 180A-180D. In another example, one or more data couplings 180A-180D can include at least a portion of network 220.

Figure 10:
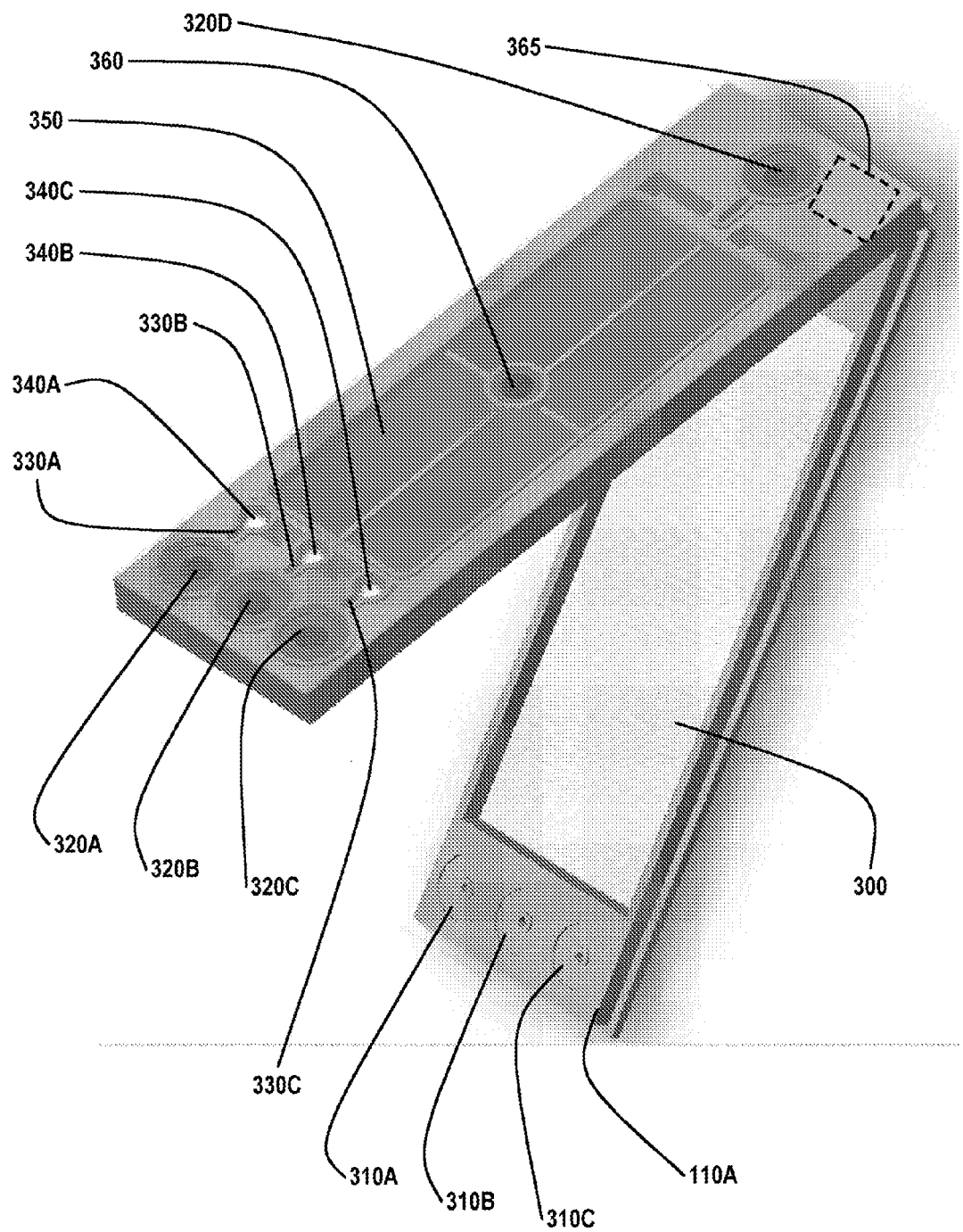
FIG. 10 is a diagram of an open self-contained sample processing receptacle in accordance with an embodiment of the present invention.

Referring now to FIG. 10, a self-contained sample processing receptacle for processing a slide is depicted in accordance with an embodiment. As shown, self-contained sample processing receptacle 110A can include a chamber 300 and fluidic valves 310A-310C coupled to chamber 300. In various embodiments, fluids (e.g., reagents, air, buffers, water, etc.) can enter through one or more of fluidic valves 310A-310C and flow into chamber 300. In other embodiments, valve control elements 320A-320C can be coupled to respective valves 310A-310C, and valve control elements 320A-320C can control flow of various fluids into chamber 300.

Valve control elements 320A-320C can be controlled pneumatically, hydraulically, mechanically, and/or magnetically, among others, and can, respectively, actuate valves 310A-310C. For example, valve controller 320A can include a magnetic material. For instance, when a magnetic field is introduced, a force can be applied to the magnetic material causing valve controller 320A to open or close valve 310A. In various embodiments, the magnetic material can include one or more magnets. In some embodiments, valve control elements 320A-320C can include one or more elastomer elements (e.g., elastomer membranes) that can place a respective valve in a default or resting position (e.g., open, closed, partially open, partially closed, etc.). In some embodiments, an auto-staining module (e.g., one of 105A-105T) can include one or more magnetic field generators (e.g., coils operable to conduct electric current, thereby generating at least one magnetic, etc.), which when actuated, can introduce a magnetic field to a respective valve control element of valve control elements 320A-320C adjusting a respective valve. For example, a respective valve can be opened or closed.

According to some embodiments, self-contained sample processing receptacle 110A can include one or more channels 330A-330C that couple and/or connect a respective valve of valves 310A-310C to chamber 300. As one of skill in the art will appreciate the location and number of the channels and valves can vary in accordance with system requirements and remain within the scope of the present disclosure. As shown, one or more of channels 330A-330C can be configured to include respective beads 340A-340C. In some embodiments, one or more of beads 340A-340C can include inert and/or reagent material.

Additionally, self-contained sample processing receptacle 110A can include an elastomer element 350 as a flexible membrane or some other appropriate flexible membrane. For example, elastomer element 350 can include an elastomer diaphragm. In some embodiments, elastomer element 350 can be operable to agitate and/or mix contents of chamber 300. For example, agitating and/or mixing the contents using elastomer element 350 can be implemented and/or controlled pneumatically, hydraulically, mechanically, and/or magnetically, among others. For example, self-contained sample processing receptacle 110A can include an actuating element 360 coupled to elastomer element 350. For example, actuating element 360 can include a magnetic material. For example, when a magnetic field is introduced and/or applied, a force can be applied to the magnetic material causing elastomer element 350 to move and/or change shape. In one or more embodiments, the magnetic material can include one or more magnets. An auto-staining module (e.g., one of 105A-105T) can include a magnetic field generator (e.g., a coil operable to conduct electric current, thereby generating at least one magnetic, etc.), which when actuated, can introduce a magnetic field to actuating element 360 and resultant forces applied to actuating element 360 can cause elastomer element 350 to move and/or change shape. For example, a magnetic field introduced and/or applied to actuating element 360 can vary at one or more frequencies. This can cause at least a portion of the contents of chamber 300 to be agitated and/or mixed.

In one or more embodiments, self-contained sample processing receptacle 110A can be configured to prevent cross contamination of one specimen with another specimen. For example, self-contained sample processing receptacle 110A can include an O-ring that seals contents of self-contained sample processing receptacle 110A. In various embodiments, self-contained sample processing receptacle 110A can be hermetically sealed.

In various embodiments, self-contained sample processing receptacle 110A can include a computer-readable identification (ID) 365. ID 365 can be disposed on and/or within self-contained sample processing receptacle 110A. The position of the ID 365 is agnostic to the location as shown. More particularly, as one of skill in the art will appreciate, ID 365 can be in several locations on self-contained sample processing receptacle 110A and stay within scope of the disclosure herein. In some embodiments, ID 365 can include one or more of a computer-readable color, hologram, bar code (e.g., one or multiple dimensions), one or more symbols, and/or a radio frequency identification (RFID) tag. For example, identification information can be determined based on information received from ID 365. In various embodiments, the determined identification information can be used to determine one or more specimen auto-staining procedures from two or more possible specimen auto-staining procedures.

In some embodiments, ID 365 can include an integrated circuit device, e.g., a processor coupled to a memory medium, radio frequency logic, one or more rectifiers, one or more sensors, one or more antennas, digital signal processing (DSP) logic, one or more modulators, etc. In some embodiments, ID 365 can be passive, active, or a combination of passive and active (e.g., semi-active or semi-passive). In one example, ID 365 can be passive and not have an on-board power source. ID 365 can be configured to use power emitted from a reader to communicate identification information with the reader. ID 365 can be in contact with the reader, or not be in such contact. In a second example, ID 365 can be active which includes an on-board power source (e.g., battery, solar cell, fuel cell, etc.). In a third example, ID 365 can be semi-active or semi-passive which can include an on-board power source for specific tasks. In various embodiments, ID 365 can be read only (RO), write once read many (WORM), or read write (RW). In some embodiments, ID 365 can include an ISO 7816 interface.

Figure 11:
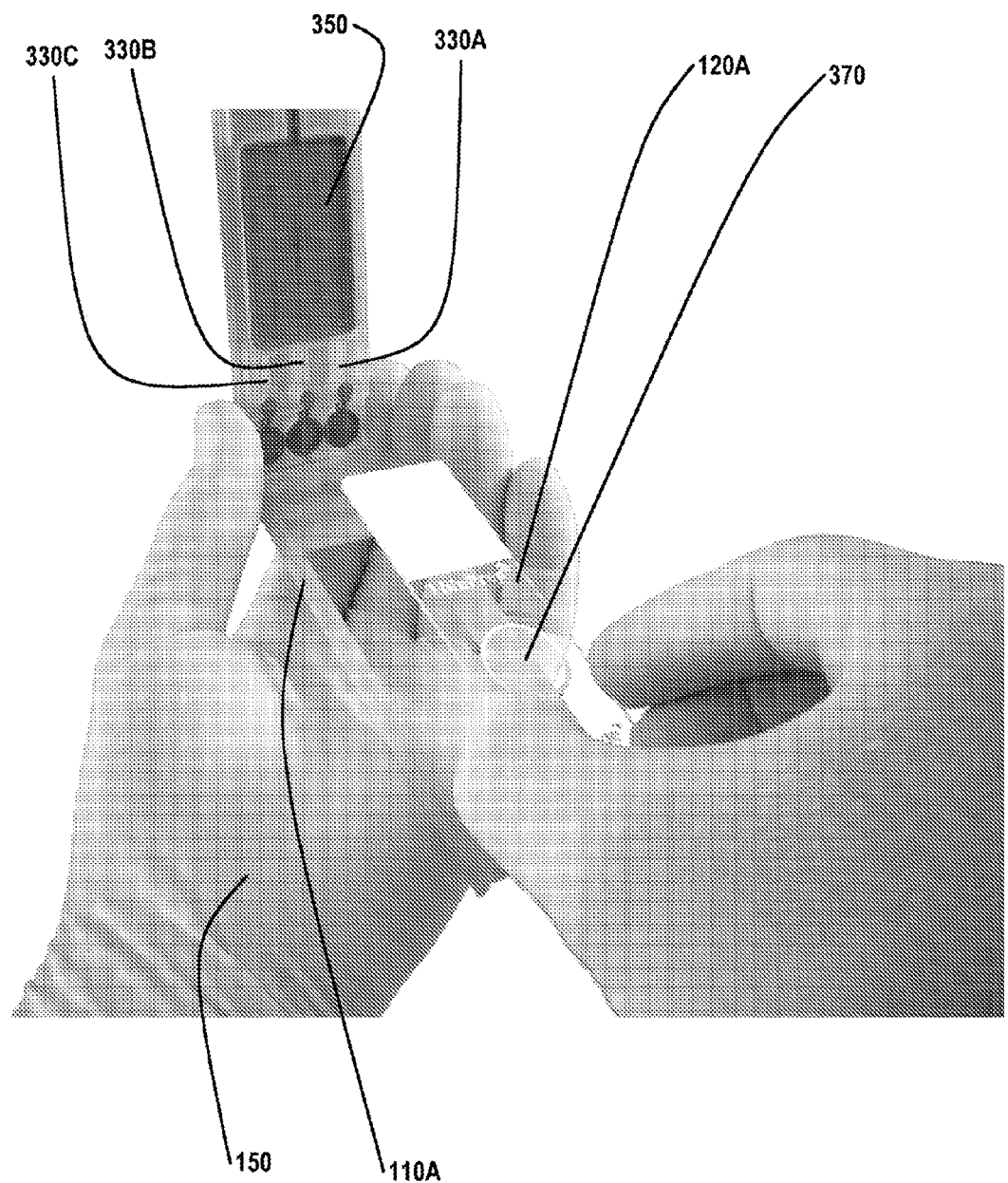
FIG. 11 is a diagram of an open self-contained sample processing receptacle with a sample being inserted in accordance with an embodiment of the present invention.
Figure 12:
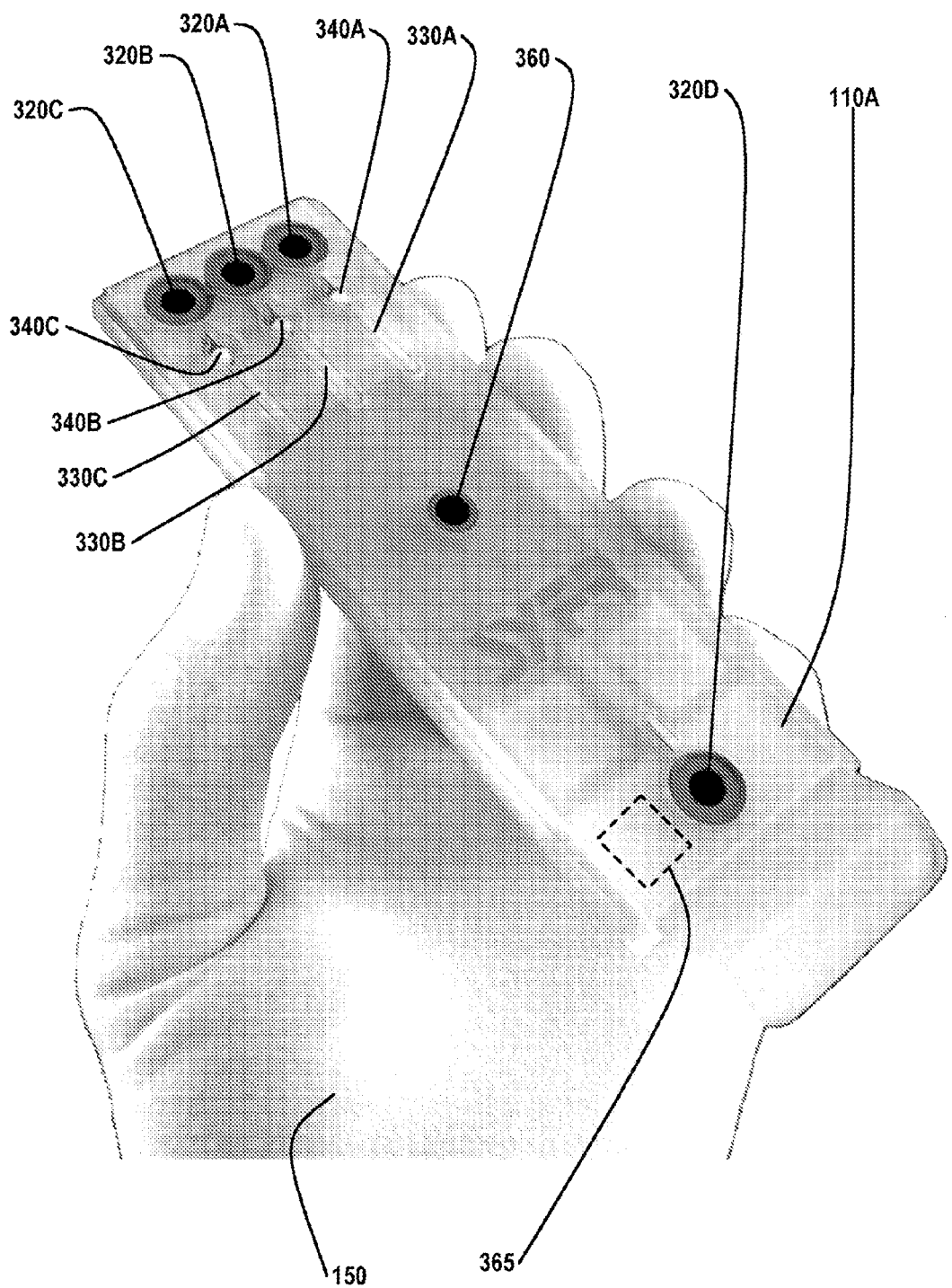
FIG. 12 is a diagram of a closed self-contained sample processing receptacle in accordance with an embodiment of the present invention.

Referring now to FIGS. 11 and 12, further details of a self-contained sample processing receptacle are depicted, according to various embodiments. As shown in FIG. 11, self-contained sample processing receptacle 110A can be configured and/or operable to receive slide 120A, and slide 120A can include a biological sample 370. Sample 370 is shown disposed on slide 120A. For example, sample 370 can include one or more of a biological sample from any species wherein the sample can include one or more of tissue, cells, a cell suspension, a block of tissues, an embedded cell suspension, a cell pellet, and/or a smear of body fluid, among others.

Figure 13:
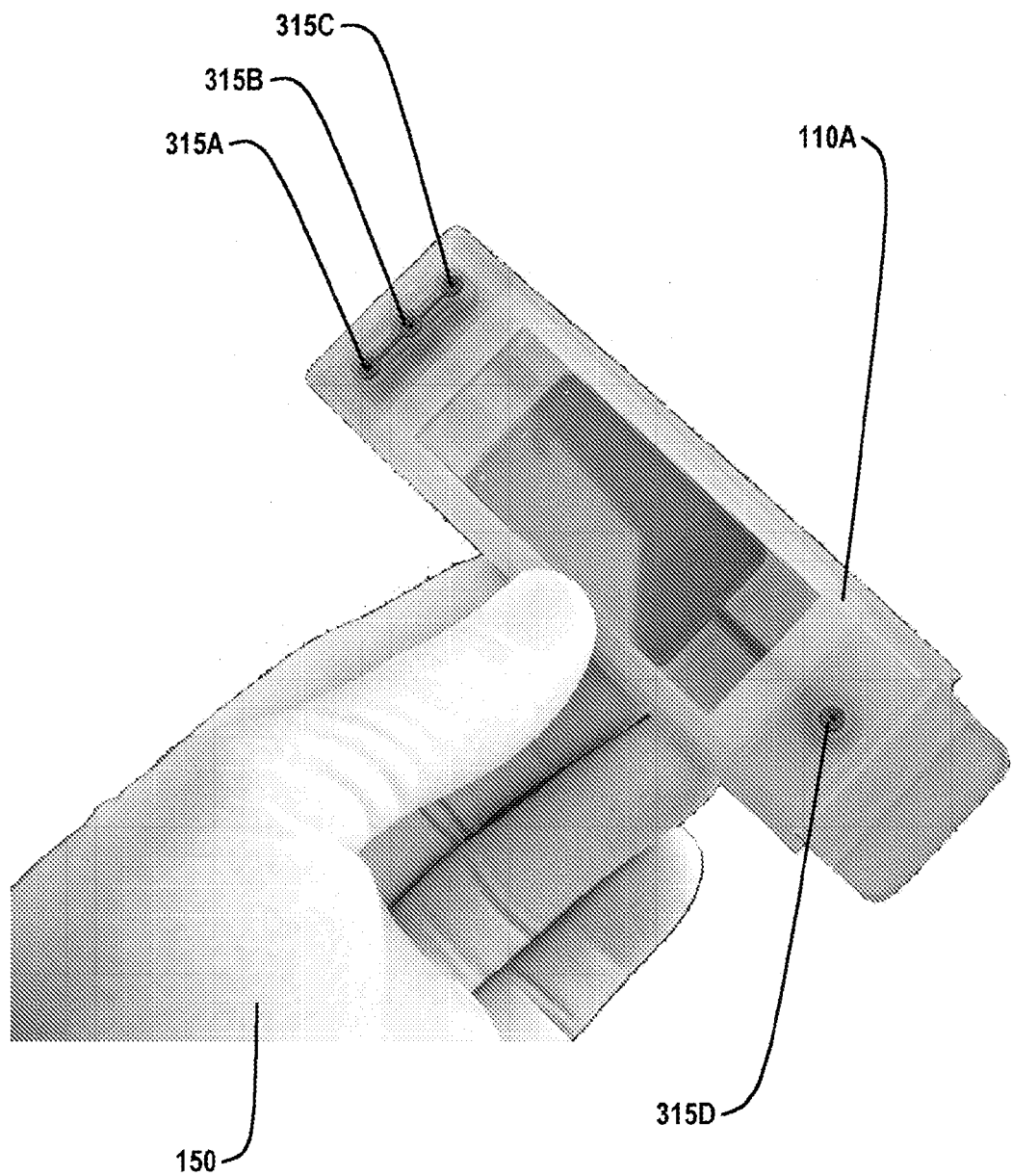
FIG. 13 is a diagram of a back side of a closed self-contained sample processing receptacle in accordance with an embodiment of the present invention.

Referring now to FIG. 13, a bottom side of a self-contained sample processing receptacle is depicted, according to various embodiments. As shown, self-contained sample processing receptacle 110A can include fluidic connectors 315A-315D that can be coupled to respective fluidic valves 310A-310C and 320D shown in FIG. 10. In various embodiments, fluids can enter self-contained sample processing receptacle 110A through one or more of fluidic connectors 315A-315C and can exit self-contained sample processing receptacle 110A through fluidic connector 315D. In some embodiments, one or more of fluidic connectors 315A-315D can interface and/or couple to an auto-staining module (e.g., auto-staining module 105B).

Turning now to FIG. 14, a cross-sectional view of an auto-staining module is depicted, according to various embodiments. As shown, auto-staining module 105B can include a water line 400 that can be coupled to fluidic connector or port 160B, a reagent line 410 that can be coupled to fluidic connector or port 160A, and a waste manifold 420 that can be coupled to fluidic connector or port 160C. In some embodiments, water line 400, reagent line 410, and waste manifold 420 can also be coupled to one or more other auto-staining modules such as one or more of auto-staining module 105A and 105C-105J. In various embodiments, auto-staining module 105B can include a check-valve 430A coupled to reagent line 410 and/or can include a check-valve 430B coupled to waste manifold 420. In some embodiments, auto-staining module 105B can include one or more magnetic field generators such as magnetic field generators 440A-440C. For example, magnetic field generators 440A-440C can include various coils that can produce various magnetic fields. Auto-staining module 105B can include a bay or module door 450. In some embodiments, module door 450 can be latched or unlatched by a user (e.g., operator 150). For example, the user can latch module door 450 after a self-contained sample processing receptacle (e.g., self-contained sample processing receptacle 110A) is placed in auto-staining module 105B and can unlatch module door 450 after one or more auto-staining procedures have completed. In various embodiments, module door 450 can be automatically latched or unlatched by one or more systems and/or methods described herein. As shown, auto-staining module 105B can include a pump 455. For example, pump 455 can be or include a peristaltic pump. In various embodiments, pump 455 can pump contents of chamber 300 to and/or through waste manifold 420.

As illustrated, auto-staining module 105B can include a thermal unit 460. In various embodiments, thermal unit 460 can be used to heat and/or cool contents of self-contained sample processing receptacle 110A. For example, thermal unit 460 can include one or more electrically resistive elements that can allow thermal unit 460 to raise a temperature. In another example, thermal unit 460 can include a thermo electric device to raise and/or lower a temperature. For instance, the thermo electric device can include one or more semi-conductive and/or bi-metallic elements which can use and/or implement a Peltier effect.

As shown, module 105B can include a chamber 480. In some embodiments, auto-staining module 105B can include various fins 470A-470C coupled to thermal unit 460. As shown, fins 470A-470C can be disposed in chamber 480. In various embodiments, chamber 480 can enclose and/or include a fluid. For example, air, water, or oil can be enclosed in chamber 480, and the air, water, or oil can surround fins 470A-470C. In various embodiments, fins 470A-470C surrounded by fluid can modulate and/or moderate temperature changes of thermal unit 460. For example, it can be desired to provide gradual temperature changes to the contents of self-contained sample processing receptacle 105A, where "gradual" can be a measure according to some metric.

Figure 15B:
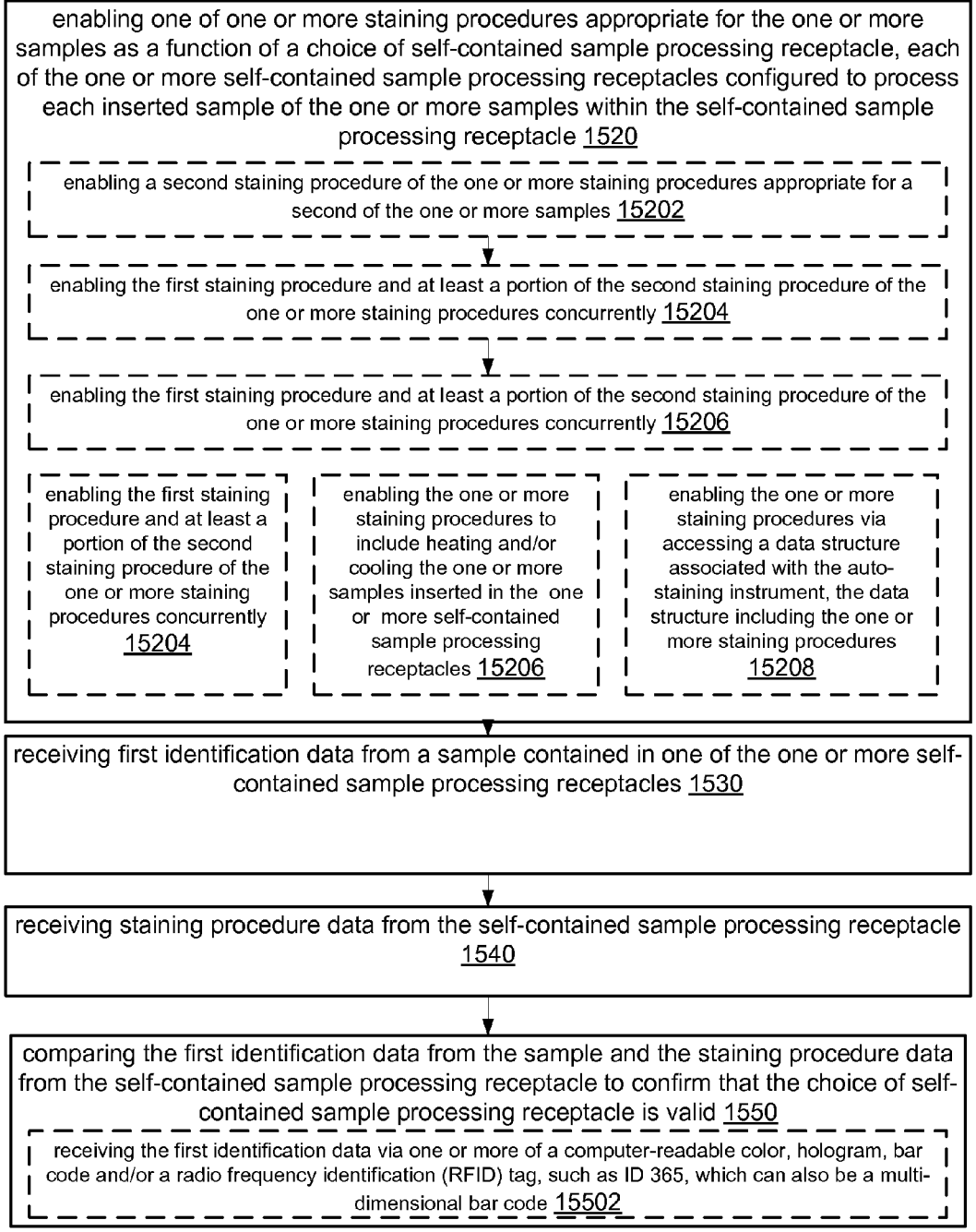
FIG. 15 is a flow diagram illustrating a method in accordance with an embodiment of the present invention.

Referring now to FIG. 15, a flow diagram is depicts a method in accordance with one or more embodiments. More specifically, block 1510 depicts providing one or more self-contained sample processing receptacles, each of the one or more self-contained sample processing receptacles configured to be inserted into an auto-staining instrument. For example, self-contained sample processing receptacle 105A can be inserted into an auto-staining instrument.

Within block 1510 is optional block 15102 which depicts providing one or more modules within the auto-staining instrument, each module operable to receive one of the one or more self-contained sample processing receptacles and independently couple each self-contained sample processing receptacle to the auto-staining instrument. For example, auto-staining instrument 100A-100C including modules such as 105B to receive self-contained sample processing receptacle 110A.

Also within block 1510 is optional block 15104 which depicts providing within each of the one or more self-contained sample processing receptacles a chamber adapted to receive and enclose at least one of the one or more samples, the chamber including a flexible membrane operable to agitate contents in the chamber. For example self-contained sample processing receptacle 110A including chamber 300 as shown in FIG. 10.

Further within optional block 15104 is shown optional block 151042 which depicts that providing one or more fluidic valves coupled to the chamber, the one or more fluidic valves enabling a pump to control flow of one or more fluids through the chamber (e.g., fluidic valves 310A-310C shown in FIG. 10).

Within optional block 151042 is further optional block 151044 which depicts providing one or more channels disposed between at least one fluidic valve of the one or more fluidic valves and the chamber, at least one of the one or more channels configured to include a reagent bead. For example, as shown in FIG. 10, self-contained sample processing receptacle 110A can include channels 330A-330C that couple and/or connect valves 310A-310C to chamber 300, and channels 330A-330C can include respective beads 340A-340C. In some embodiments, one or more of beads 340A-340C can include inert and/or reagent material. The one or more channels can be adapted to enable dissolving the reagent bead via one or more of agitating and/or pumping.

Further depicted within optional block 151042 is optional block 151046 which provides for enabling performance of the one or more staining procedures via pumping a fluid through the chamber and through at least one of the one or more fluidic valves, the at least one of the one or more fluidic valves coupled to a magnetic element responsive to a magnetic field generator of the auto-staining instrument, the magnetic element actuating the at least one of the one or more fluidic valves. The enabling performance can include enabling evacuation of at least a portion of contents of the chamber. For example, as shown in FIGS. 10 and 13, fluids can enter self-contained sample processing receptacle 110A through one or more of fluidic connectors 315A-315C and can exit self-contained sample processing receptacle 110A through a fluidic connector.

Further depicted within optional block 151042 is optional block 151046 which provides for providing the one or more fluidic valves as peristaltic pumps and/or operable with one or more pumps associated with the auto-staining instrument. For example, fluidic connectors 315A-315C can operate as peristaltic pumps alone or with other pumps in or outside the auto-staining instrument.

Further disposed within block 1510 is block 15106 which depicts providing within each of the one or more self-contained sample processing receptacles a magnetic element coupled to the elastomer element, the magnetic element responsive to a magnetic field generator disposed within one or more of the auto-staining instrument and/or a module disposed within the auto-staining instrument, the magnetic element adapted to cause agitation of the chamber using the elastomer element when the magnetic field generator is activated, the magnetic field generator adapted to produce one or more magnetic fields that apply force to the magnetic element, whereby the elastomer element responds.

Also disposed within block 1510 is optional block 15108 which provides for hermetically sealing at least one of the one or more self-contained sample processing receptacles. For example, self-contained sample processing receptacle 110A can be configured to prevent cross contamination of one specimen with another specimen via an O-ring that seals contents of self-contained sample processing receptacle 110A and/or by being hermetically sealed.

Block 1520 provides for enabling one of one or more staining procedures appropriate for the one or more samples as a function of a choice of self-contained sample processing receptacle, each of the one or more self-contained sample processing receptacles configured to process each inserted sample of the one or more samples within the self-contained sample processing receptacle. For example, referring to FIG. 2, user 150 chooses a self-contained sample processing receptacle 110A wherein each self-contained sample processing receptacle 110A is capable of self-containing one of a plurality of different reagents for different staining procedures.

Disposed within block 1520 is optional block 15202 and block 15204. Block 15202 provides for enabling a first staining procedure of the one or more staining procedures appropriate for a first of the one or more samples. For example, self-contained sample processing receptacle 110A can self-contain a first staining procedure. Block 15204 provides for enabling a second staining procedure of the one or more staining procedures appropriate for a second of the one or more samples. For example, self-contained sample processing receptacle 110B can self-contain a second staining procedure within the same auto-staining instrument 100A or 100B. Block 15204 is followed by optional block 15206 which provides for enabling the first staining procedure and at least a portion of the second staining procedure of the one or more staining procedures concurrently. For example, auto-staining unit 100A or 100B can perform auto-staining of different procedures independently.

Block 1520 further includes optional block 15206, which provides for enabling the one or more staining procedures to include heating and/or cooling the one or more samples inserted in the one or more self-contained sample processing receptacles. For example, as shown in FIG. 14, auto-staining module 105B can include a thermal unit 460 that can be used to heat and/or cool contents of self-contained sample processing receptacle 110A. For example, thermal unit 460 can include one or more electrically resistive elements that can allow thermal unit 460 to raise a temperature or a thermo electric device to raise and/or lower temperature.

Block 1520 further includes optional block 15208 which provides for enabling the one or more staining procedures via accessing a data structure associated with the auto-staining instrument, the data structure including the one or more staining procedures. In one embodiment, the enabling the one or more staining procedures via accessing a data structure associated with the auto-staining instrument, includes accessing the data structure including accessing a database.

Block 1530 provides for receiving first identification data from a sample contained in one of the one or more self-contained sample processing receptacles. For example, each sample can be a biological sample on a slide or other physical medium. Each slide or other physical medium can have an identification thereon. Referring back to FIGS. 11 and 12, as shown, sample 370 can include one or more of a biological sample from any species wherein the sample can include one or more of tissue, cells, a cell suspension, a block of tissues, an embedded cell suspension, a cell pellet, and/or a smear of body fluid, among others.

Block 1540 provides for receiving staining procedure data from the self-contained sample processing receptacle. For example, each self-contained processing receptacle 105 can include a computer-readable identification, such as an RFID tag or the like that can communicate the type of procedure that can be performed by the self-contained sample processing receptacle 105. For example, self-contained sample processing receptacle 110A can include a computer-readable identification (ID) 365. ID 365 can be disposed on and/or within self-contained sample processing receptacle 110A. In some embodiments, ID 365 can include one or more of a computer-readable color, hologram, bar code or the like.

Block 1550 provides for comparing the first identification data from the sample and the staining procedure data from the self-contained sample processing receptacle to confirm that the choice of self-contained sample processing receptacle is valid. The comparison can operate as a check for user 150 prior to running any procedure. More specifically, after a user 150 inserts a sample into a self-contained sample processing receptacle, and the sample and self-contained sample processing receptacle are inserted into auto-staining instrument, the auto-staining system can address a database holding data concerning each procedure with a list of appropriate samples. For example, FIG. 7 illustrates memory mediums 177A-177C, and FIG. 9 illustrates database 240.

Depicted within block 1550 is optional block 15502, which provides for receiving the first identification data via one or more of a computer-readable color, hologram, bar code (e.g., a one or more dimensional bar code) and/or a radio frequency identification (RFID) tag, such as ID 365.

Figure 16:
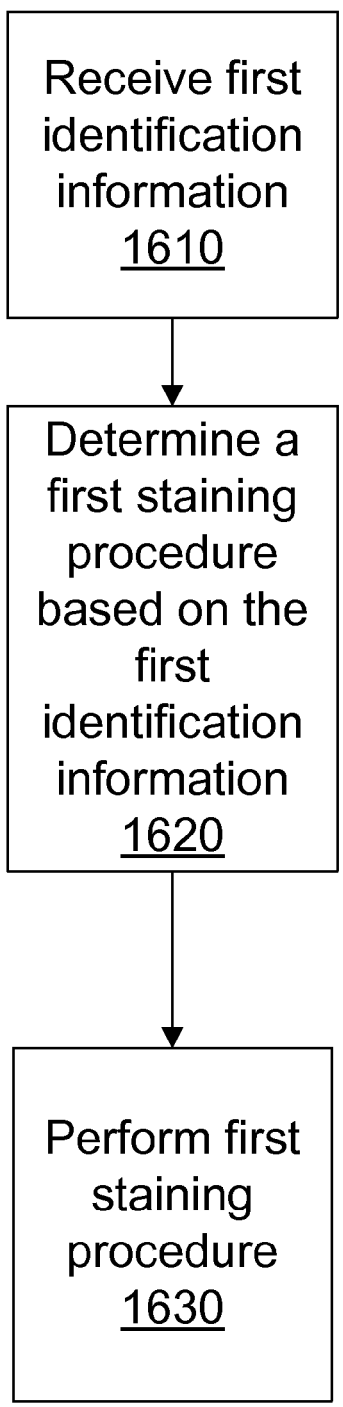
FIG. 16 is a flow diagram illustrating a method in accordance with an embodiment of the present invention.

Referring now to FIG. 16, another flow diagram illustrates a method in accordance with an embodiment. Block 1610 provides for receiving first identification information. In one example, auto-staining instrument 100A can receive the first identification information via auto-staining module 105B. In another example, one or more of PCD 230A, DTCD 230B, SCD 230C, and/or database 240 can receive the first identification information. In various embodiments, identification information (e.g., first identification information, second identification information, third identification information, etc.) can be received from one or more of a computer-readable color, hologram, bar code and/or a radio frequency identification (RFID) tag, among others, included on and/or within a first self-contained sample processing receptacle (e.g., self-contained sample processing receptacle 110A). Next, block 1620 provides for determining a first sample auto-staining based on the first identification information. In various embodiments, one or more sample auto-staining procedures can be determined based on the first identification information. For example, Table 1, below, shows various possible identifications associated with various possible auto-staining procedures.

Next, at 1630, a first sample staining procedure may be determined based on the first identification information. In various embodiments, one or more sample staining procedures may be determined based on the first identification information. For example, Table 1 shows various possible identifications associated with various possible staining procedures.

TABLE 1

| | |
|---|---|
| Identification A | Staining Procedure B, Staining Procedure D |
| Identification B | Staining Procedure A |
| Identification C | Staining Procedure D, Staining Procedure B |
| Identification D | Staining Procedure C, Staining Procedure A, Staining Procedure E |
| Identification E | Staining Procedure B |
| Identification F | Staining Procedure A |

In various embodiments, information associated with Table 1 may be stored in a data structure that may be stored in a memory medium that may be accessed by one or more of instrument units 100A-100C, PCD 230A, DTCD 230B, SCD 230C, and/or database 240 to determine a staining procedure (e.g., the first staining procedure, etc.). For example, referring to FIG. 7, the data structure may be stored in one or more of memory mediums 177A-177C. In another example, the data structure may be stored in a memory medium included in one or more of PCD 230A, DTCD 230B, SCD 230C, and/or database 240 as shown in FIG. 9. In some embodiments, the portions of the data structure may be distributed among two or more of memory mediums 177A-177C and memory mediums of DTCD 230B, SCD 230C, and/or database 240. In some embodiments, the data structure may be indexed based on information associated with the first identification information.

Next, at block 1630, the first staining procedure can be performed.

Figure 17:
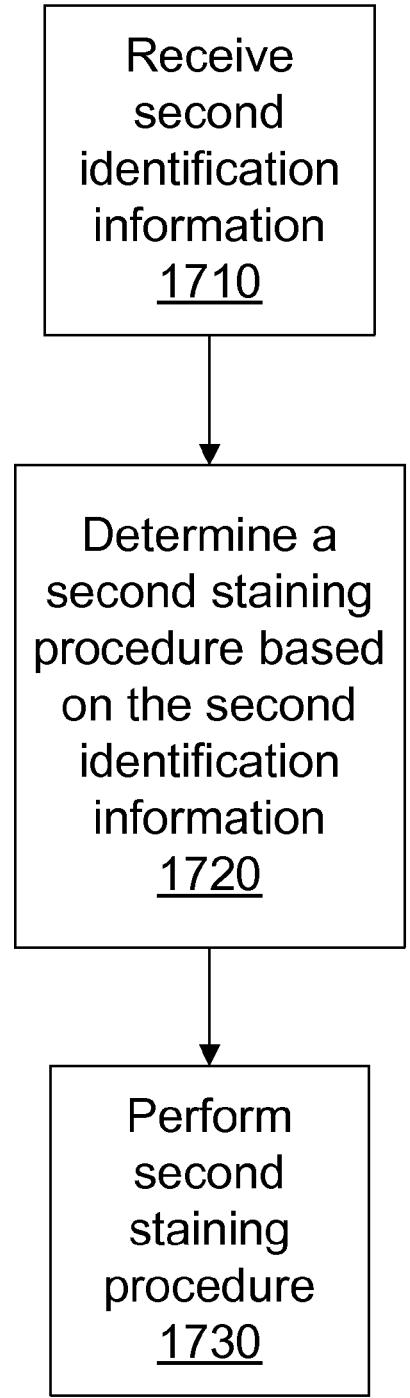
FIG. 17 is a flow diagram illustrating a method in accordance with an embodiment of the present invention.

Turning now to FIG. 17, a flow diagram is depicted, according to various embodiments. At 1710, second identification information may be received. For example, the second identification information may be received from a second self-contained sample processing receptacle (e.g., 110B). In various embodiments, the second identification information may be different from the first identification information or the second identification information may be the same as the first identification information. In one example, instrument unit 100A (FIG. 2) may receive the second identification information via staining module 105C. In a second example, instrument unit 100B may receive the second identification information via staining module 105K. In another example, one or more of PCD 230A, DTCD 230B, SCD 230C, and/or database 240 (FIG. 9) may receive the second identification information.

Next, at 1720, a second sample staining procedure may be determined based on the second identification information. In various embodiments, two or more sample staining procedures may be determined based on the second identification information. In some embodiments, various methods, data structures, memory mediums, and/or systems associated with block 1620 may be used to realize and/or implement block 1720 by using the second identification information in place of the first identification information.

In some embodiments, blocks 1620 and 1720 may determine the same staining procedure even when the first identification information and the second identification information differ. For example, referring to Table 1, the first identification information may be associated with "Identification F" and the second identification information may be associated with "Identification B", and each of "Identification F" and "Identification B" is associated with "Staining Procedure A". This may allow various systems and/or methods described herein to be configurable. For instance, "Identification F" may have been previously associated with "Staining Procedure C", and various systems and/or methods described herein have been configured to associate "Identification F" with "Staining Procedure A". This may be more desirable than configuring or re-configuring identifications on various self-contained sample processing receptacles. For example, one or more of the identifications of respective self-contained sample processing receptacles 110A-110F may be read-only, and it may not be possible to change their identification information. In another example, one or more of the identifications of respective self-contained sample processing receptacles 110A-110F may include read-write capabilities, and it may be time-consuming to re-configure a number of self-contained sample processing receptacles.

Next, at 1730, the second staining procedure may be performed.

In various embodiments, staining instruments 100A-100C, PCD 230A, DTCD 230B, SCD 230C, and/or database 240 may execute instructions that implement various methods and/or portions of various methods described herein in a concurrent fashion. In one example, time slicing may be used to provide an apparent simultaneous performance of two or more tasks by a computer system. In another example, two or more tasks may be performed in parallel by one or more computer systems. In some embodiments, concurrent processing may include executing two or more tasks in parallel and/or in an apparent simultaneous performance of two or more tasks by computer system. For example, a scheduler may be implemented that may allow multi-tasking and/or time slicing to occur. For instance, the scheduler may allow execution of processes in a round robin and/or priority fashion, among others. In some embodiments, two or more virtual machines may be implemented that may allow multi-tasking to occur.

In various embodiments, a computer system may include various components that may implement concurrency. For example, one or more of instrument units 100A-100C, PCD 230A, DTCD 230B, SCD 230C, and/or database 240 may include a direct memory access (DMA) controller. For instance, a DMA controller of instrument unit 100B may be used to transfer data between instrument units 100A and 100C with minimal or no instruction execution by processor 175B of instrument unit 100B.

Figure 18:
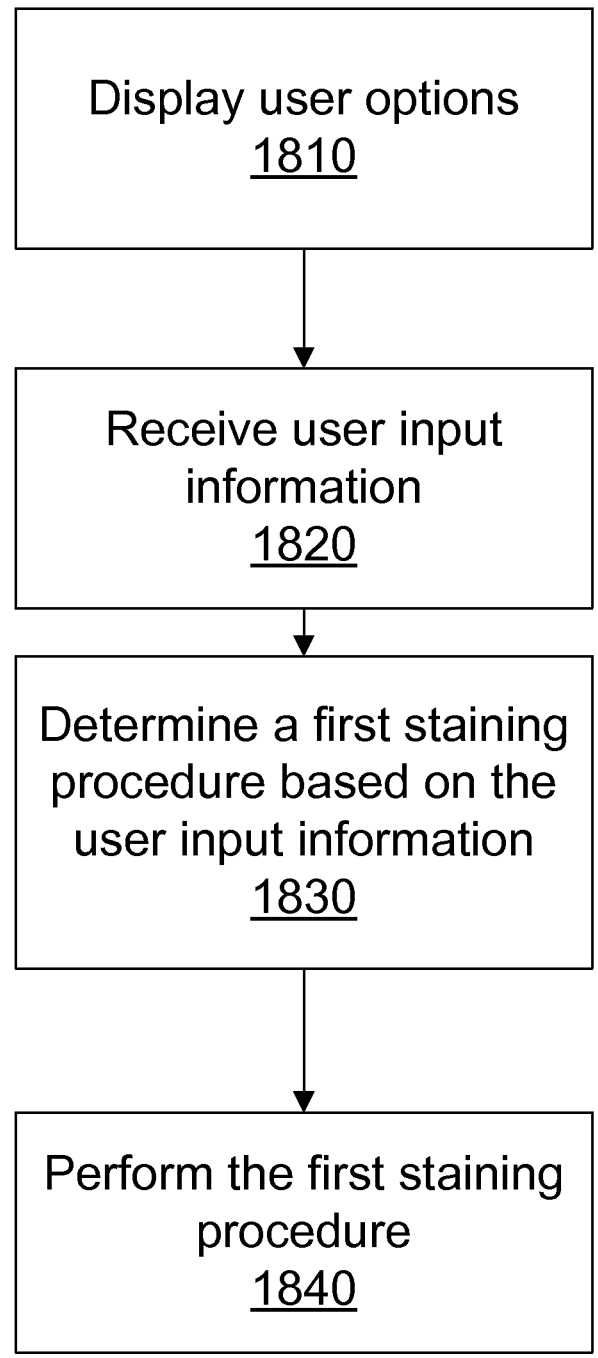
FIG. 18 is a flow diagram illustrating a method in accordance with an embodiment of the present invention.

Referring now to FIG. 18, a flow diagram of a staining procedure is depicted, according to various embodiments. In various embodiments, user input may be used in determining one or more staining procedures to be performed. At 1810, various options can be communicated to a user (e.g., operator 150). In various embodiments, a user interface may be used to communicate information to a user and/receive information from the user. In some embodiments, the user interface may include a display unit that may be used to display options to the user. For example, the display unit can include one or more of a screen, a liquid crystal display (LCD), an organic light emitting diode (OLED) display, and/or any device operable to convey information to the user. For instance, one or more of PCD 230A, DTCD 230B, and/or SCD 230C may display the options to the user.

Next, at 1050, user input information may be received, where the user input information is associated with one or more sample staining procedures. In various embodiments, one or more of staining modules 105A-105T, instrument units 100A-100C, PCD 230A, DTCD 230B, and/or SCD 230C may receive the user input information via a user interface. For example, the user interface may include one or more of buttons, keys of a keyboard, a mouse, a graphical user interface (GUI), a voice interface, a gesture interface, a smart-card interface, a touch screen, a joy stick, and/or anything that would allow a human to interface with a computer system.

For example, the user may select one or more staining procedures associated with an identification shown in Table 1. In some embodiments, the user may select one or more staining procedures which may not be available in Table 1. In one example, the user may select "Staining Procedure E", "Staining Procedure A", "Staining Procedure C" which is a reverse order of staining procedures associated with identification information "Identification D". In another example, the user may select "Staining Procedure D" and "Staining Procedure C". In various embodiments, the user input may override identification information received from a computer-readable color, hologram, bar code and/or a radio frequency identification (RFID) tag, among others, included on and/or within a cartridge (e.g., self-contained sample processing receptacle 110A).

Next, at 1060, a first sample staining procedure may be determined based on the user input information, and, at 1840, the first sample staining procedure may be performed.

Figure 19:
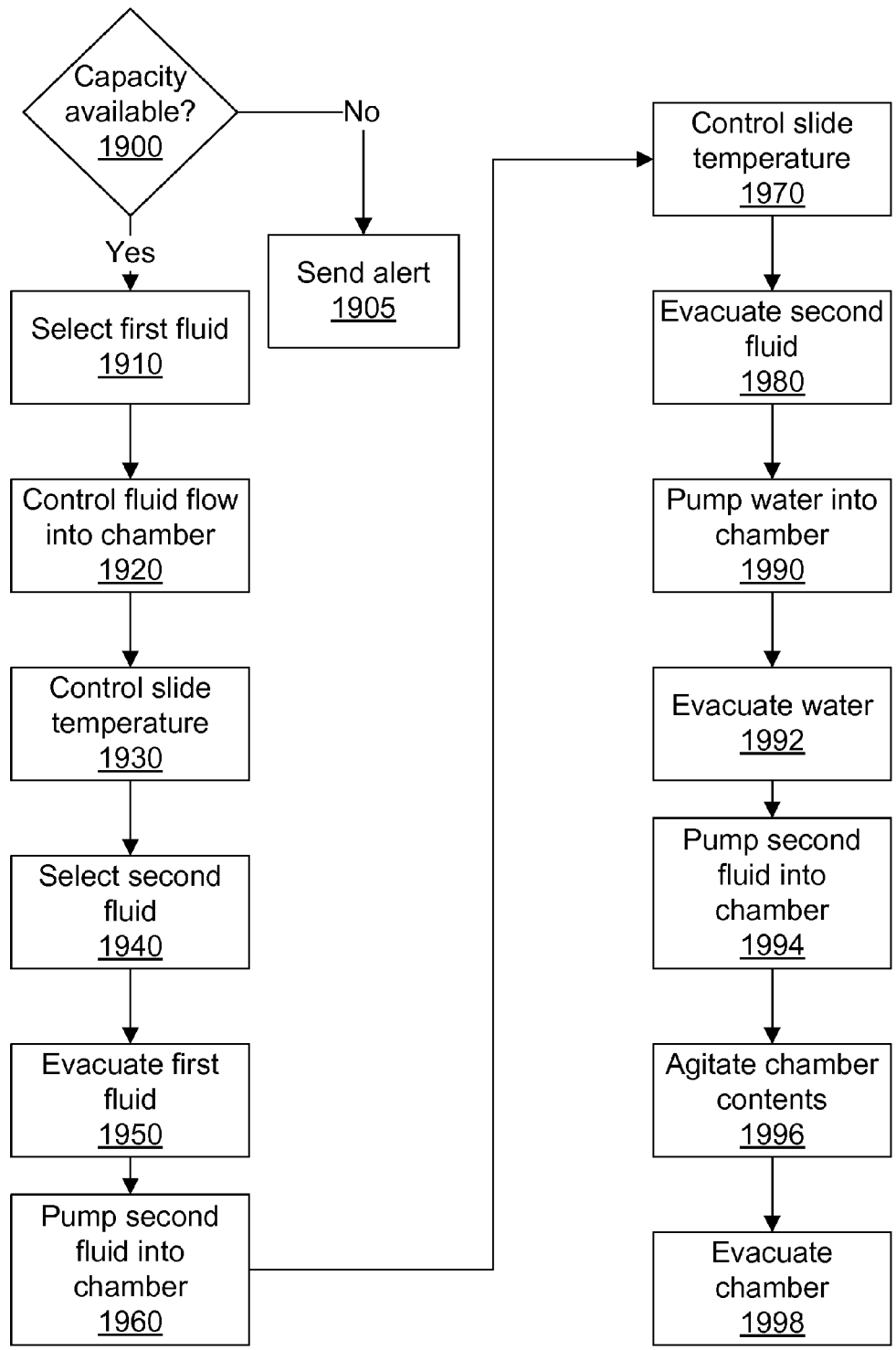
FIG. 19 is a flow diagram illustrating a method in accordance with an embodiment of the present invention.

Referring now to FIG. 19, a flow diagram depicts a staining procedure, according to various embodiments. At 1900, one or more amounts of respective one or more reservoirs 130A-130I may be determined. For instance, various capacities of reservoirs may be required for the staining procedure. For example, the staining procedure may need a first amount from reservoir 130A and a second amount from reservoir 130C. The first and second amounts may be the same or different. The staining procedure may need a capacity available in a reservoir, e.g., in one or more of waste reservoirs 130G-130I. In some embodiments, instrument unit 100A may not be coupled a waste reservoir configured to receive a type of waste generated by the staining procedure, even though various required reagents are available. Thus, it may not have a capacity for that type of waste.

If capacity is not available, an alert may be sent at 1905. For example, instrument unit 100A may indicate visual and/or audio information about the determination from 1900. In another example, a message, that may include information associated with the determination at 1900, may be transmitted to a computer system, pager, mobile telephone, etc.

If capacity is available, the staining procedure may proceed to 1910, where a first fluid may be selected through fluidic selection device 210. For example, fluidic selection device 210 may receive selection information, and fluidic selection device 210 may select a fluid based on the selection information. Next, at 1920, the first fluid (e.g., from reservoir 130C) can be controlled into a chamber 300 via fluidic valve 310A and channel 330A. Next, at 1930, a temperature of a slide in the chamber may be controlled. In various embodiments, the temperature control may lower or raise temperature. Moreover, the temperature control may adjust temperature to and maintained at a level for a period of time. In some embodiments, the temperature control may include adjusting temperature to one level for a period of time and then adjusting temperature to another level for another period of time. For example, the slide may be heated and/or cooled.

Next, a second fluid may be selected at 1940. Similar to what is described above, fluidic selection device 210 may select and deliver fluid from reservoir 130A to staining instrument 100A. At 1950, the first fluid may be evacuated from chamber 300, and at 1960, the second fluid may be pumped into chamber 300 via fluidic valve 310B and channel 330B. In some embodiments, the first fluid may be evacuated from chamber 300 while the second fluid is being pumped into chamber 300. In various embodiments, evacuating a fluid from chamber 300 may occur through gravity, a vacuum pumping action, and/or by the introduction of pressure from an incoming fluid.

Next, at 1970, a temperature of a slide in the chamber may be controlled. At 1980, the second fluid may be evacuated from chamber 300, and at 1990 water may be pumped into chamber 300. In some embodiments, the second fluid may be evacuated from chamber 300 while the water is being pumped into chamber 300. In some embodiments, flushing the chamber may include pumping in water, air, a neutralizing agent, and/or a sterilizing agent. Next, at 1992, the water may be evacuated from chamber 300, and, at 1994 the second fluid may be pumped into chamber 300 via fluidic valve 310A and channel 330C which may include a reagent bead 340C. In various embodiments, the second fluid flowing through channel 330C may cause one or more portions of reagent bead 340C to dissolve. In some embodiments, the water may be evacuated from chamber 300 while the second fluid is being pumped into chamber 300.

Next, at 1996, contents of chamber 300 may be agitated and/or mixed. As described above, the cartridge may include an elastomer element and a magnetic material. In some embodiments, the magnetic material may include a magnet. In various embodiments, a staining module may apply a magnetic field that varies at one or more frequencies. The magnetic field may cause forces to be applied to the magnetic material and, thus, to the elastomer element which causes the contents of the chamber to be agitated and/or mixed. In some embodiments, agitating and/or mixing the contents of chamber 300 may cause one or more portions of reagent bead 340C to dissolve and/or mixed with the contents of chamber 300.

At 1998, the chamber may be evacuated. In various embodiments, air may be allowed to enter the chamber so a vacuum may not be created. In some embodiments, one or more portions of the contents of chamber 300 may be evacuated through fluidic valve 310D.

It is noted that in various embodiments of one or more of the method elements may be performed concurrently, performed rapidly enough to be viewed as concurrent to a user, in a different order, or be omitted. Additional elements may be performed as desired.

While the subject matter of the application has been shown and described with reference to particular embodiments thereof, it will be understood by those skilled in the art that the foregoing and other changes in form and detail can be made therein without departing from the spirit and scope of the subject matter of the application, including but not limited to additional, less or modified elements and/or additional, less or modified steps performed in the same or a different order.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and/or analog communication links using TDM (time division multiplexing) or IP (Internet protocol) based communication links (e.g., packet links).

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

We claim:

1. A system for automatic staining of one or more biological samples, the system comprising:
   an auto-staining instrument, wherein the auto-staining instrument is configured to receive one or more sample processing receptacles and comprises fluidic ports and a reader, the reader being configured to obtain an identification of at least one pre-loaded reagent from the one or more sample processing receptacles when the one or more sample processing receptacles are received within the auto-staining instrument;
   the one or more sample processing receptacles, wherein each of the one or more sample processing receptacles includes fluid valves, the at least one pre-loaded reagent, and a sealable chamber for sheathing the one or more biological samples to be stained;
   reservoirs containing staining procedure fluids coupled to the auto-staining instrument via the fluidic ports of the auto-staining instrument, wherein the fluidic ports are further coupled to the fluidic valves of each of the one or more sample processing receptacles to provide the staining procedure fluids from the reservoirs to the chamber of each of the one or more sample processing reservoirs;
   a processor coupled to the auto-staining instrument;
   a memory coupled to the processor, the memory encoded with instructions that when executed by the processor comprise the steps of:
      accessing a plurality of sample processing procedures;
      determining one or more sample processing procedures from the plurality of sample processing procedures appropriate for the one or more sample processing receptacles based on the identification of the at least one pre-loaded reagent from the one or more sample processing receptacles, and
      commanding staining of the one or more biological samples within the one or more sample processing receptacles.

2. The system of claim 1 wherein the memory is further encoded with instructions that when executed by the processor comprise the step of comparing identification data from the one or more biological samples with staining procedure data from the one or more sample processing receptacles to confirm that the one or more sample processing receptacles are appropriate for the one or more biological samples.

3. The system of claim 1 wherein the auto-staining instrument is daisy-chained to at least a second auto-staining instrument, the second auto-staining instrument configured to receive at least one of the one or more sample processing receptacles.

4. The system of claim 1 further comprising at least one waste reservoir that receives waste fluids that exit from the one or more sample processing receptacles.

\* \* \* \* \*